Figure 1:
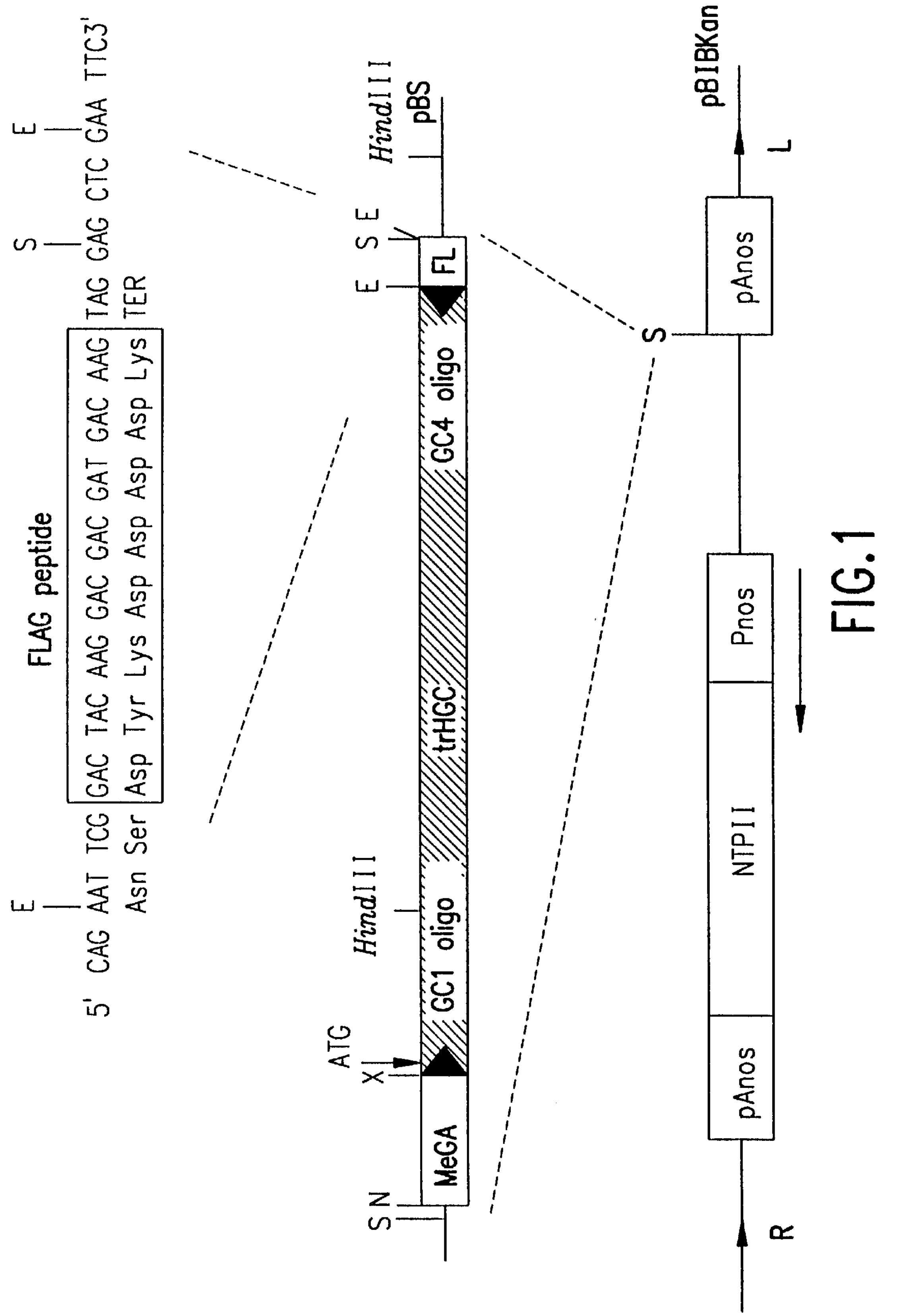

US005929304A

United States Patent [19]

Radin et al.

[11] Patent Number: 5,929,304

[45] Date of Patent: Jul. 27, 1999

[54] PRODUCTION OF LYSOSOMAL ENZYMES IN PLANT-BASED EXPRESSION SYSTEMS

[75] Inventors: David N. Radin; Carole L. Cramer; Karen K. Oishi; Deborah L. Weissenborn, all of Blacksburg, Va.

[73] Assignees: Croptech Development Corporation; Virginia Tech Intellectual Properties, Inc.

[21] Appl. No.: 08/713,928

[22] Filed: Sep. 13, 1996

Related U.S. Application Data

[60] Provisional application No. 60/003,737, Sep. 14, 1995.

[51] Int. Cl.[6] .............................. C12N 5/14; C12N 15/52; C12N 15/63

[52] U.S. Cl. .......................... 800/288; 800/278; 800/287; 800/294; 800/295; 800/317.3; 435/69.1; 435/410; 435/414; 435/183; 435/206; 435/320.1; 536/23.1; 536/23.2; 536/24.1

[58] Field of Search ................................ 435/69.1, 320.1, 435/410, 414, 183, 206; 800/205, 250, 255, 278, 294, 287, 295, 288, 317.3; 536/23.2, 24.1, 23.1

[56] References Cited

U.S. PATENT DOCUMENTS

| | | | |
|---|---|---|---|
| 5,057,422 | 10/1991 | Bol et al. | 435/325 |
| 5,349,122 | 9/1994 | Hain et al. | 800/205 |
| 5,422,108 | 6/1995 | Mirkov et al. | 424/94.61 |
| 5,543,576 | 8/1996 | van Ooijen et al. | 800/250 |
| 5,550,038 | 8/1996 | Goodman et al. | 435/70.1 |

FOREIGN PATENT DOCUMENTS

WO 93/24630 12/1993 WIPO .

OTHER PUBLICATIONS

Ameis et al., 1994, *Eur. J. Biochem.* 219;905–914.

Ausubel et al., eds., 1989, *Current Protocols in Mol. Biol.*, vol. I Green Pub. Assoc., Inc. & J. Wiley & Sons, Inc., N.Y., pp. 2.10.1–2.10.3.

Berg–Fussman et al., 1993, *J. Biol. Chem.* 268:14861–14866.

Chrispeels, 1991, *Annu. Rev. Plant Physiol. Plan. Biol.* 42:21–53.

Cramer et al., 1996, "High–level of enzymatically active human lysosomal proteins in transgenic tobacco", *Transgenic Plants: A production system for industrial and pharmaceutical proteins*, eds., Owens & Pen, J. Wiley & Sons.

Daniele et al., 1993, *Genomics* 16:755–757.

de Wet et al., 1984, *DNA* 3:437–447.

Eng & Desnick, 1994, *Hum. Mutat.* 3:103–111.

Erickson et al., 1985, *J. Biol. Chem.* 260:14319–14324.

Ferrari et al., 1994, *Glycobiol.* 4:2047–2052.

Furbish et al., 1977, *PNAS USA* 74:3560–3563.

Furbish et al., 1981, *Biochem. Biophys. Acta* 673:425–434.

Grabowski et al., 1989, *Enzyme* 41:131–142.

Grace & Grabowski, 1990, *Biochem. Biophys. Res. Comm.* 168:771–777.

Grace et al., 1990, *J. Biol. Chem.* 265:6827–6835.

Grace et al., 1994, *J. Biol. Chem.* 269:2283–2291.

Haskins et al., 1979, *Pediat. Res.* 13:1294–1297.

Hopp et al., 1988, *Bio/Tech.* 6:1204–1210.

Jonsson et al, 1987, *Eur. J. Biochem.* 164:171–179.

Kakkis et al., 1995, *Am. J. Hum. Genet.* 57:A39 (Abstr. No. 193).

Kaplan et al., 1977, *PNAS USA* 74:2026–2030.

Kornfeld & Mellman, 1989, *Ann. Rev. Cell Biol.* 5:483–525.

Moskowitz et al., 1992, *FASEB J.* 6:A77 (Abstr. No. 445).

Murray, 1987, *Methods in Enzymol.* 149:25–42.

Park et al., 1992, *Plant Mol. Biol.* 20:327–331.

Schatzle et al., 1992, *J. Biol. Chem.* 267:4000–4007.

Scott et al., 1991, *PNAS USA* 88:9695–9699.

Scott et al., 1992, *Genomics* 13:1311–1313.

G.S. Shelness, 1992, *Epitope* 1:11–12, 17.

Shull et al., 1994, *PNAS USA* 91:12937–12941.

Sijmons et al., 1990, *Biotech.* 8:217–221.

Sorge et al., 1985, *PNAS USA* 82:7289–7293.

Thornburg et al., 1987, *PNAS USA* 84:744–748.

Tsuji et al., 1986, *J. Biol. Chem.* 261:50–53.

Vandekerckhove et al., 1989, *Biotech.* 7:929–932.

von Figura & Hasilik, 1986, *Annu. Rev. Biochem.* 55:167–193.

Warner et al., 1990, *Biochem. Biophys. Res. Comm.* 173:13–19.

Weissenborn et al., 1995, *Phys. Plantarum* 93:393–400.

Zhu & Goldstein, 1993, *Gene* 137:309–314.

International Search Report, Application No. PCT/US96/14730.

Schulz et al., Principles of Protein Structure, Springer–Verlag, New York, pp. 14–16, 1979.

Ngo et al., The Protein Folding Problem and Tertiary Structure Prediction, Merz et al., eds., Birkhauser, Boston, pp. 492–495, 1994.

Wells, Biochemistry 29:8509–8517, Sep. 1990.

Bowie et al., Science 247:1306–1310, 1990.

*Primary Examiner*—Elizabeth Kemmerer
*Attorney, Agent, or Firm*—Pennie & Edmonds LLP

[57] ABSTRACT

The invention relates to the production of enzymatically active recombinant human and animal lysosomal enzymes involving construction and expression of recombinant expression constructs comprising coding sequences of human or animal lysosomal enzymes in a plant expression system. The plant expression system provides for post-translational modification and processing to produce a recombinant gene product exhibiting enzymatic activity. The invention is demonstrated by working examples in which transgenic tobacco plants having recombinant expression constructs comprising human hGC and IDUA nucleotide sequences produced enzymatically active modified human glucocerebrosidase and human α-L-iduronidase. The recombinant lysosomal enzymes produced in accordance with the invention may be used for a variety of purposes, including but not limited to enzyme replacement therapy for the therapeutic treatment of human and animal lysosomal storage diseases.

73 Claims, 29 Drawing Sheets

FIG.2A
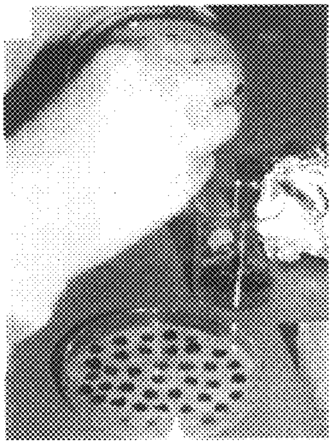
FIG.2B
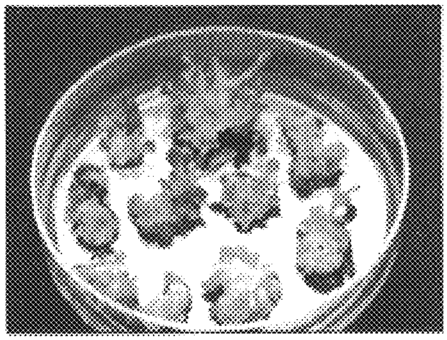
FIG.2C
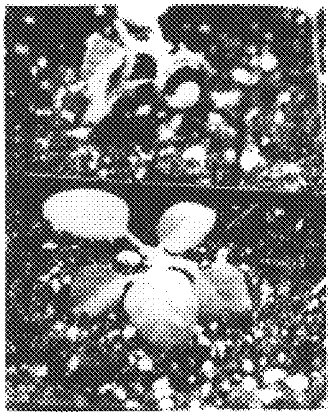
FIG.2D
FIG.2E

FIG.9A

```
                                     123 ATGGAGTT TTCAAGTCCT TCCAGAGAGG
151  AATGTCCCAA GCCTTTGAGT AGGGTAAGCA TCATGGCTGG CAGCCTCACA
201  GGTTTGCTTC TACTTCAGGC AGTGTCGTGG GCATCAGGTG CCCGCCCCTG
251  CATCCCTAAA AGCTTCGGCT ACAGCTCGGT GGTGTGTGTC TGCAATGCCA
301  CATACTGTGA CTCCTTTGAC CCCCCGACCT TTCCTGCCCT TGGTACCTTC
351  AGCCGCTATG AGAGTACACG CAGTGGGCGA CGGATGGGGC TGAGTATGGG
401  GCCCATCCAG GCTAATCACA CGGGCACAGG CCTGCTACTG ACCCTGCAGC
451  CAGAACAGAA GTTCCAGAAA GTGAAGGGAT TTGGAGGGGC CATGACAGAT
501  GCTGCTGCTC TCAACATCCT TGCCCTGTCA CCCCCTGCCC AAAATTTGCT
551  ACTTAAATCG TACTTCTCTG AAGAAGGAAT CGGATATAAC ATCATCCGGG
601  TACCCATGGC CAGCTGTGAC TTCTCCATCC GCACCTACAC CTATGCAGAC
651  ACCCCTGATG ATTTCCAGTT GCACAACTTC AGCCTCCCAG AGGAAGATAC
701  CAAGCTCAAG ATACCCCTGA TTCACCGAGC CCTGCAGTTG GCCCAGCGTC
```

```
751   CCGTTTCACT CCTTGCCAGC CCCTGGACAT CACCCACTTG GCTCAAGACC
801   AATGGAGCGG TGAATGGGAA GGGGTCACTC AAGGGACAGC CCGGAGACAT
851   CTACCACCAG ACCTGGGCCA GATACTTTGT GAAGTTCCTG GATGCCTATG
901   CTGAGCACAA GTTACAGTTC TGGGCAGTGA CAGCTGAAAA TGAGCCTTCT
951   GCTGGGCTGT TGAGTGGATA CCCCTTCCAG TGCCTGGGCT TCACCCCTGA
1001  ACATCAGCGA GACTTCATTG CCCGTGACCT AGGTCCTACC CTCGCCAACA
1051  GTACTCACCA CAATGTCCGC CTACTCATGC TGGATGACCA ACGCTTGCTG
1101  CTGCCCCACT GGGCAAAGGT GGTACTGACA GACCCAGAAG CAGCTAAATA
1151  TGTTCATGGC ATTGCTGTAC ATTGGTACCT GGACTTTCTG GCTCCAGCCA
1201  AAGCCACCCT AGGGGAGACA CACCGCCTGT TCCCCAACAC CATGCTCTTT
1251  GCCTCAGAGG CCTGTGTGGG CTCCAAGTTC TGGGAGCAGA GTGTGCGGCT
1301  AGGCTCCTGG GATCGAGGGA TGCAGTACAG CCACAGCATC ATCACGAACC
1351  TCCTGTACCA TGTGGTCGGC TGGACCGACT GGAACCTTGC CCTGAACCCC
```

FIG.9B

```
1401  GAAGGAGGAC CCAATTGGGT GCGTAACTTT GTCGACAGTC CCATCATTGT
1451  AGACGTCACC AGGGACACGT TTTACAAACA GCCCATGTTC TACCACCTTG
1501  GCCACTTCAG CAAGTTCATT CCTGAGGGCT CCCAGAGAGT GGGGCTGGTT
1551  GCCAGTCAGA AGAACGACCT GGACGCAGTG GCACTGATGC ATCCCGATGG
1601  CTCTGCTGTT GTGGTCGTGC TAAACCGCTC CTCTAAGGAT GTGCCTCTTA
1651  CCATCAAGGA TCCTGCTGTG GGCTTCCTGG AGACAATCTC ACCTGGCTAC
1701  TCCATTCACA CCTACCTGTG GCGTCGCCAG aattcggact acaaggacga
1751  cgatgacaag tTGA
```

FIG.9C 1 50
MEFSSPSREE CPKPLSRVS IMAGSLTGLL LLQAVSWASG ARPCIPKSFG
51 100
YSSVVCVCNA TYCDSFDPP TFPALGTFSR YESTRSGRRM ELSMGPIQAN
101 150
HTGTGLLLTL QPEQKFQKV KGFGGAMTDA AALNILALSP PAQNLLLKSY
151 200
FSEEGIGYNI IRVPMASCD FSIRTYTYAD TPDDFQLHNF SLPEEDTKLK
201 250
IPLIHRALQL AQRPVSLLA SPWTSPTWLK TNGAVNGKGS LKGQPGDIYH
251 300
QTWARYFVKF LDAYAEHKL QFWAVTAENE PSAGLLSGYP FQCLGFTPEH
301 350
QRDFIARDLG PTLANSTHH NVRLLMLDDQ RLLLPHWAKV VLTDPEAAKY
351 400
VHGIAVHWYL DFLAPAKAT LGETHRLFPN TMLFASEACV GSKFWEQSVR
401 450
LGSWDRGMQY SHSIITNLL YHVVGWTDWN LALNPEGGPN WVRNFVDSPI
451 500
IVDVTKDTFY KQPMFYHLG HFSKFIPEGS QRVGLVASQK NDLDAVALMH
501 550
PDGSAVVVVL NRSSKDVPL TIKDPAVGFL ETISPGYSIH TYLWRRQnsd
ykddddk"

FIG.10

```
                                                            60
CAATACGATA TTACCGAATA TTATACTAAA TCAAAATTTA ATTTATCATA TCGAATTATT

                                                           120
AAACTGATAT TTCAAATTTT AATATTTAAT ATCTACTTTC AACTATTATT ACCTAATTAT

                                                           180
CAAATGCAAA ATGTATGAGT TATTTCATAA TAGCCCGAGT TCGTATCCAA ATATTTTACA

                                                           240
CTTGACCAGT CAACTTGACT ATATAAAACT TTACTTCAAA AAATTAAAAA AAAAAGAAAG

                                                           300
TATATTATTG TAAAAGATAA TACTCCATTC AAAATATAAA ATGAAAAAAG TCCAGCGCGG

                                                           360
CAACCGGGTT CCTCTATAAA TACATTTCCT ACATCTTCTC TTCTCCTCAC ATCCCATCAC

                                                           420
TCTTCTTTTA ACAATTATAC TTGTCAATCA TCAATCCCAC AAACAACACT TTTTCTCTCC

                                                   471
TCTTTTTCCT CACCGGCGGC AGACTTACCG GTGAAATCTA GAGTAAGCAT C
```

FIG. 11

FIG. 13A
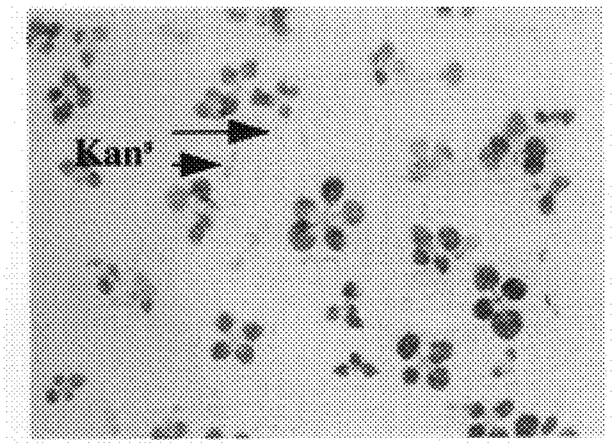
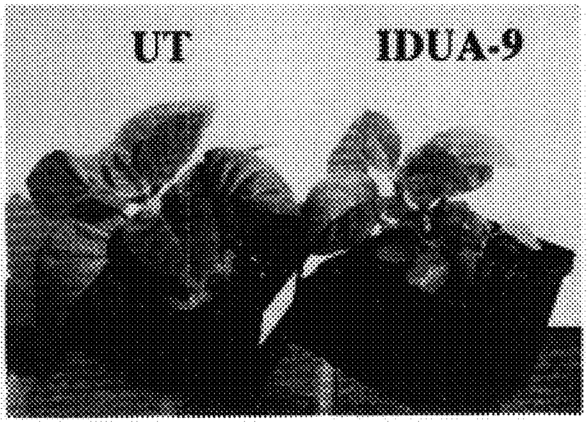
FIG. 13B
FIG. 13C

```
                         90                  110
                         ATGCGTCCCCTGCGCCCCCGCGCCGCGCTGCT

        130                   150                  170
GGCGCTCCTGGCCTCGCTCCTGGCCGCGCCCCCGGTGGCCCCGGCCGAGGCCCCGCACCT

        190                   210                  230
GGTGCAGgTGGACGCGGCCCGCGCGCTGTGGCCCCTGCGGCGCTTCTGGAGGAGCACAGG

        250                   270                  290
CTTCTGCCCCCCGCTGCCACACAGCCAGGCTGACCAGTACGTCCTCAGCTGGGACCAGCA

        310                   330                  350
GCTCAACCTCGCCTATGTGGGCGCCGTCCCTCACCGCGGCATCAAGCAGGTCCGGACCCA

        370                   390                  410
CTGGCTGCTGGAGCTTGTCACCACCAGGGGGTCCACTGGACGGGGCCTGAGCTACAACTT

        430                   450                  470
CACCCACCTGGACGGGTACTTGGACCTTCTCAGGGAGAACCAGCTCCTCCCAGGGTTTGA
```

FIG.19A

```
490                     510                     530
GCTGATGGGCAGCGCCTCGGGCCACTTCACTGACTTTGAGGACAAGCAGCAGGTGTTTGA

550                     570                     590
GTGGAAGGACTTGGTCTCCAGCCTGGCCAGGAGATACATCGGTAGGTACGGACTGGCGCA

610                     630                     650
TGTTTCCAAGTGGAACTTCGAGACGTGGAATGAGCCAGACCACCACGACTTTGACAACGT

670                     690                     710
CTCCATGACCATGCAAGGCTTCCTGAACTACTACGATGCCTGCTCGGAGGGTCTGCGCGC

730                     750                     770
CGCCAGCCCCGCCCTGCGGCTGGGAGGCCCCGGCGACTCCTTCCACACCCCACCGCGATC

790                     810                     830
CCCGCTGAGCTGGGGCCTCCTGCGCCACTGCCACGACGGTACCAACTTCTTCACTGGGGA
```

FIG.19B

FIG.19C

```
     850                 870                 890
GGCGGGCGTGCGGCTGGACTACATCTCCCTCCACAGGAAGGGTGCGCGCAGCTCCATCTC

     910                 930                 950
CATCCTGGAGCAGGAGAAGGTCGTCGCGCAcgAGATCCGGCAGCTCTTCCCCAAGTTCGC

     970                 990                1010
GGACACCCCCATTTACAACGACGAGGCGGACCCGCTGGTGGGCTGGTCCCTGCCACAGCC

    1030                1050                1070
GTGGAGGGCGGACGTGACCTACGCGGCCATGGTGGTGAAGGTCATCGCGCAGCATCAGAA

    1090                1110                1130
CCTGCTACTGGCCAACACCACCTCCGCCTTCCCCTACGCGCTCCTGAGCAACGACAATGC

    1150                1170                1190
CTTCCTGAGCTACCACCCGCACCCCTTCGCGCAGCGCACGCTCACCGCGCGCTTCCAGGT

    1210                1230                1250
CAACAACACCCGCCCGCCGCACGTGCAGCTGTTGCGCAAGCCGGTGCTCACGGCCATGGG
```

```
      1270                    1290                    1310
GCTGCTGGCGCTGCTGGATGAGGAGCAGCTCTGGGCCGAAGTGTCGCAGGCCGGGACCGT

      1330                    1350                    1370
CCTGGACAGCAACCACACGGTGGGCGTCCTGGCCAGCGCCCACCGCCCCCAGGGCCCGGC

      1390                    1410                    1430
CGACGCCTGGCGCGCCGCGGTGCTGATCTACGCGAGCGACGACACCCGCGCCCACCCCAA

      1450                    1470                    1490
CCGCAGCGTCGCGGTGACCCTGCGGCTGCGCGGGGTGCCCCCCGGCCCGGGCCTGGTCTA

      1510                    1530                    1550
CGTCACGCGCTACCTGGACAACGGGCTCTGCAGCCCCGACGGCGAGTGGCGGCGCCTGGG

      1570                    1590                   1610
CCGGCCCGTCTTCCCCACGGCAGAGCAGTTCCGGCGCATGCGCGCGGCTGAGGACCCGGT
```

FIG.19D

FIG.19E

```
       1630                1650                1670
GGCCGCGGCGCCCCGCCCCTTACCCGCCGGCGGCCGCCTGACCCTGCGCCCCGCGCTGCG

       1690                1710                1730
GCTGCCGTCGCTTTTGCTGGTGCACGTGTGTGCGCGCCCCGAGAAGCCGCCCGGGCAGGT

       1750                1770                1790
CACGCGGCTCCGCGCCCTGCCCCTGACCCAAGGGCAGCTGGTTCTGGTCTGGTCGGATGA

       1810                1830                1850
ACACGTGGGCTCCAAGTGCCTGTGGACATACGAGATCCAGTTCTCTCAGGACGGTAAGGC

       1870                1890                1910
GTACACCCCGGTCAGCAGGAAGCCATCGACCTTCAACCTCTTTGTGTTCAGCCCAGACAC

       1930                1950                1970
AGGTGCTGTCTCTGGCTCCTACCGAGTTCGAGCCCTGGACTACTGGGCCCGACCAGGCCC

       1990                2010                2030
CTTCTCGGACCCTGTGCCGTACCTGGAGGTCCCTGTGCCAAGAGGGCCCCCATCCCCGGG
```

```
        2050                2070                2090
CAATCCATGAGCCTGTGCTGAGCCCCAGTGGGTTGCACCTCCACCGGCAGTCAGCGAGCT

        2110                2130                2150
GGGGCTGCACTGTGCCCATGCTGCCCTCCCATCACCCCCTTTGCAATATATTTTT
```

FIG.19F

FIG.20A

```
         10                  30                  50
MRPLRPRAALLALLASLLAAPPVAPAEAPHLVHVDAARALWPLRRFWRSTGFCPPLPHSQ

         70                  90                 110
ADQYVLSWDQQLNLAYVGAVPHRGIKQVRTHWLLELVTTRGSTGRGLSYNFTHLDGTLDL

        130                 150                 170
LRENQLLPGFELMGSASGHFTDFEDKQQVFEWKDLVSSLARRYIGRYGLAHVSKWNFETW

        190                 210                 230
NEPDHHDFDNVSMTMQGFLNYYDACSEGLRAASPALRLGGPGDSFHTPPRSPLSWGLLRH

        250                 270                 290
CHDGTNFFTGEAGVRLDYISLHRKGARSSISILEQEKVVAQEIRQLFPKFADTPIYNDEA

        310                 330                 350
DPLVGWSLPQPWRADVTYAAMVVKVIAQHQNLLLANTTSAFPYALLSNDNAFLSYHPHPF

        370                 390                 410
AQRTLTARFQVNNTRPPHVQLLRKPVLTAMGLLALLDEEQLWAEVSQAGTVLDSNHTVGV
```

```
       430                 450                 470
LASAHRPQGPADAWRAAVLIYASDDTRAHPNRSVAVTLRLRGVPPGPGLVYVTRYLDNGL

       490                 510                 530
CSPDGEWRRLGRPVFPTAEQFRRMRAAEDPVAAAPRPLPAGGRLTLRPALRLPSLLLVHV

       550                 570                 590
CARPEKPPGQVTRLRALPLTQGQLVLVWSDEHVGSKCLWTYEIQFSQDGKAYTPVSRKPS

       610                 630                 650
TFNLFVFSPDTGAVSGSYRVRALDYWARPGPFSDPVPYLEVPVPRGPPSPGNP
```

FIG.20B

```
SEQUENCE LISTING

(1) GENERAL INFORMATION:

   (iii) NUMBER OF SEQUENCES: 15

(2) INFORMATION FOR SEQ ID NO:1:

     (i) SEQUENCE CHARACTERISTICS:
          (A) LENGTH: 27 base pairs
          (B) TYPE: nucleic acid
          (C) STRANDEDNESS: single
          (D) TOPOLOGY: unknown

    (ii) MOLECULE TYPE: other nucleic acid
          (A) DESCRIPTION: /desc = "PCR primer"

    (xi) SEQUENCE DESCRIPTION: SEQ ID NO:1:

TTGTCTAGAG TAAGCATCAT GGCTGGC                                    27

(2) INFORMATION FOR SEQ ID NO:2:

     (i) SEQUENCE CHARACTERISTICS:
          (A) LENGTH: 33 base pairs
          (B) TYPE: nucleic acid
          (C) STRANDEDNESS: single
```

-continued (D) TOPOLOGY: unknown (ii) MOLECULE TYPE: other nucleic acid
(A) DESCRIPTION: /desc = "PCR primer"

(xi) SEQUENCE DESCRIPTION: SEQ ID NO:2:

CACGAATTCT GGCGACGCCA CAGGTAGGTG TGA 33

(2) INFORMATION FOR SEQ ID NO:3:

(i) SEQUENCE CHARACTERISTICS:
(A) LENGTH: 1642 base pairs
(B) TYPE: nucleic acid
(C) STRANDEDNESS: unknown
(D) TOPOLOGY: unknown (ii) MOLECULE TYPE: cDNA (xi) SEQUENCE DESCRIPTION: SEQ ID NO:3:

ATGGAGTTTT CAAGTCCTTC CAGAGAGGAA TGTCCCAAGC CTTTGAGTAG GGTAAGCATC 60

ATGGCTGGCA GCCTCACAGG TTTGCTTCTA CTTCAGGCAG TGTCGTGGGC ATCAGGTGCC 120

CGCCCCTGCA TCCCTAAAAG CTTCGGCTAC AGCTCGGTGG TGTGTGTCTG CAATGCCACA 180

TACTGTGACT CCTTTGACCC CCCGACCTTT CCTGCCCTTG GTACCTTCAG CCGCTATGAG 240

AGTACACGCA GTGGGCGACG GATGGGGCTG AGTATGGGGC CCATCCAGGC TAATCACACG 300

GGCACAGGCC TGCTACTGAC CCTGCAGCCA GAACAGAAGT TCCAGAAAGT GAAGGGATTT 360

GGAGGGGCCA TGACAGATGC TGCTGCTCTC AACATCCTTG CCCTGTCACC CCCTGCCCAA 420

AATTTGCTAC TTAAATCGTA CTTCTCTGAA GAAGGAATCG GATATAACAT CATCCGGGTA 480

CCCATGGCCA GCTGTGACTT CTCCATCCGC ACCTACACCT ATGCAGACAC CCCTGATGAT 540

TTCCAGTTGC ACAACTTCAG CCTCCCAGAG GAAGATACCA AGCTCAAGAT ACCCCTGATT 600

CACCGAGCCC TGCAGTTGGC CCAGCGTCCC GTTTCACTCC TTGCCAGCCC CTGGACATCA 660

CCCACTTGGC TCAAGACCAA TGGAGCGGTG AATGGGAAGG GGTCACTCAA GGGACAGCCC 720

GGAGACATCT ACCACCAGAC CTGGGCCAGA TACTTTGTGA AGTTCCTGGA TGCCTATGCT 780

GAGCACAAGT TACAGTTCTG GGCAGTGACA GCTGAAAATG AGCCTTCTGC TGGGCTGTTG 840

AGTGGATACC CCTTCCAGTG CCTGGGCTTC ACCCCTGAAC ATCAGCGAGA CTTCATTGCC 900

CGTGACCTAG GTCCTACCCT CGCCAACAGT ACTCACCACA ATGTCCGCCT ACTCATGCTG 960

GATGACCAAC GCTTGCTGCT GCCCCACTGG GCAAAGGTGG TACTGACAGA CCCAGAAGCA 1020

GCTAAATATG TTCATGGCAT TGCTGTACAT TGGTACCTGG ACTTTCTGGC TCCAGCCAAA 1080

GCCACCCTAG GGGAGACACA CCGCCTGTTC CCCAACACCA TGCTCTTTGC CTCAGAGGCC 1140

TGTGTGGGCT CCAAGTTCTG GGAGCAGAGT GTGCGGCTAG GCTCCTGGGA TCGAGGGATG 1200

CAGTACAGCC ACAGCATCAT CACGAACCTC CTGTACCATG TGGTCGGCTG GACCGACTGG 1260

AACCTTGCCC TGAACCCCGA AGGAGGACCC AATTGGGTGC GTAACTTTGT CGACAGTCCC 1320

ATCATTGTAG ACGTCACCAG GGACACGTTT TACAAACAGC CCATGTTCTA CCACCTTGGC 1380

CACTTCAGCA AGTTCATTCC TGAGGGCTCC CAGAGAGTGG GGCTGGTTGC CAGTCAGAAG 1440

AACGACCTGG ACGCAGTGGC ACTGATGCAT CCCGATGGCT CTGCTGTTGT GGTCGTGCTA 1500

AACCGCTCCT CTAAGGATGT GCCTCTTACC ATCAAGGATC CTGCTGTGGG CTTCCTGGAG 1560

ACAATCTCAC CTGGCTACTC CATTCACACC TACCTGTGGC GTCGCCAGAA TTCGGACTAC 1620

AAGGACGACG ATGACAAGTT GA 1642

(2) INFORMATION FOR SEQ ID NO:4:

(i) SEQUENCE CHARACTERISTICS:
(A) LENGTH: 546 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:4:

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365
```

-continued

```
Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Val Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln Asn Ser Asp Tyr Lys Asp Asp Asp
    530                 535                 540

Asp Lys
545
```

(2) INFORMATION FOR SEQ ID NO:5:

(i) SEQUENCE CHARACTERISTICS:
(A) LENGTH: 471 base pairs
(B) TYPE: nucleic acid
(C) STRANDEDNESS: unknown
(D) TOPOLOGY: unknown (ii) MOLECULE TYPE: other nucleic acid
(A) DESCRIPTION: /desc = "MeGA Promoter"

(xi) SEQUENCE DESCRIPTION: SEQ ID NO:5:

```
CAATACGATA TTACCGAATA TTATACTAAA TCAAAATTTA ATTTATCATA TCGAATTATT     60

AAACTGATAT TTCAAATTTT AATATTTAAT ATCTACTTTC AACTATTATT ACCTAATTAT    120

CAAATGCAAA ATGTATGAGT TATTTCATAA TAGCCCGAGT TCGTATCCAA ATATTTTACA    180

CTTGACCAGT CAACTTGACT ATATAAAACT TTACTTCAAA AAATTAAAAA AAAAAGAAAG    240

TATATTATTG TAAAAGATAA TACTCCATTC AAAATATAAA ATGAAAAAAG TCCAGCGCGG    300

CAACCGGGTT CCTCTATAAA TACATTTCCT ACATCTTCTC TTCTCCTCAC ATCCCATCAC    360

TCTTCTTTTA ACAATTATAC TTGTCAATCA TCAATCCCAC AAACAACACT TTTTCTCTCC    420

TCTTTTTCCT CACCGGCGGC AGACTTACCG GTGAAATCTA GAGTAAGCAT C             471
```

(2) INFORMATION FOR SEQ ID NO:6:

(i) SEQUENCE CHARACTERISTICS:
(A) LENGTH: 32 base pairs
(B) TYPE: nucleic acid
(C) STRANDEDNESS: single
(D) TOPOLOGY: unknown (ii) MOLECULE TYPE: other nucleic acid
(A) DESCRIPTION: /desc = "PCR primer"

(xi) SEQUENCE DESCRIPTION: SEQ ID NO:6:

-continued

CTAGTCTAGA ATGCGTCCCC TGCGCCCCCG CG 32

(2) INFORMATION FOR SEQ ID NO:7:

(i) SEQUENCE CHARACTERISTICS:
(A) LENGTH: 33 base pairs
(B) TYPE: nucleic acid
(C) STRANDEDNESS: single
(D) TOPOLOGY: unknown (ii) MOLECULE TYPE: other nucleic acid
(A) DESCRIPTION: /desc = "PCR primer"

(xi) SEQUENCE DESCRIPTION: SEQ ID NO:7:

GGAATTCGAG CTCTCATGGA TTGCCCGGGG ATG 33

(2) INFORMATION FOR SEQ ID NO:8:

(i) SEQUENCE CHARACTERISTICS:
(A) LENGTH: 2067 base pairs
(B) TYPE: nucleic acid
(C) STRANDEDNESS: unknown
(D) TOPOLOGY: unknown (ii) MOLECULE TYPE: cDNA (xi) SEQUENCE DESCRIPTION: SEQ ID NO:8:

ATGCGTCCCC TGCGCCCCCG CGCCGCGCTG CTGGCGCTCC TGGCCTCGCT CCTGGCCGCG 60

CCCCCGGTGG CCCCGGCCGA GGCCCCGCAC CTGGTGCAGG TGGACGCGGC CCGCGCGCTG 120

TGGCCCCTGC GGCGCTTCTG GAGGAGCACA GGCTTCTGCC CCCCGCTGCC ACACAGCCAG 180

GCTGACCAGT ACGTCCTCAG CTGGGACCAG CAGCTCAACC TCGCCTATGT GGGCGCCGTC 240

CCTCACCGCG GCATCAAGCA GGTCCGGACC CACTGGCTGC TGGAGCTTGT CACCACCAGG 300

GGGTCCACTG GACGGGGCCT GAGCTACAAC TTCACCCACC TGGACGGGTA CTTGGACCTT 360

CTCAGGGAGA ACCAGCTCCT CCCAGGGTTT GAGCTGATGG GCAGCGCCTC GGGCCACTTC 420

ACTGACTTTG AGGACAAGCA GCAGGTGTTT GAGTGGAAGG ACTTGGTCTC CAGCCTGGCC 480

AGGAGATACA TCGGTAGGTA CGGACTGGCG CATGTTTCCA AGTGGAACTT CGAGACGTGG 540

AATGAGCCAG ACCACCACGA CTTTGACAAC GTCTCCATGA CCATGCAAGG CTTCCTGAAC 600

TACTACGATG CCTGCTCGGA GGGTCTGCGC GCCGCCAGCC CCGCCCTGCG GCTGGGAGGC 660

CCCGGCGACT CCTTCCACAC CCCACCGCGA TCCCCGCTGA GCTGGGGCCT CCTGCGCCAC 720

TGCCACGACG GTACCAACTT CTTCACTGGG GAGGCGGGCG TGCGGCTGGA CTACATCTCC 780

CTCCACAGGA AGGGTGCGCG CAGCTCCATC TCCATCCTGG AGCAGGAGAA GGTCGTCGCG 840

CACGAGATCC GGCAGCTCTT CCCCAAGTTC GCGGACACCC CCATTTACAA CGACGAGGCG 900

GACCCGCTGG TGGGCTGGTC CCTGCCACAG CCGTGGAGGG CGGACGTGAC CTACGCGGCC 960

ATGGTGGTGA AGGTCATCGC GCAGCATCAG AACCTGCTAC TGGCCAACAC CACCTCCGCC 1020

TTCCCCTACG CGCTCCTGAG CAACGACAAT GCCTTCCTGA GCTACCACCC GCACCCCTTC 1080

GCGCAGCGCA CGCTCACCGC GCGCTTCCAG GTCAACAACA CCCGCCCGCC GCACGTGCAG 1140

CTGTTGCGCA AGCCGGTGCT CACGGCCATG GGGCTGCTGG CGCTGCTGGA TGAGGAGCAG 1200

CTCTGGGCCG AAGTGTCGCA GGCCGGGACC GTCCTGGACA GCAACCACAC GGTGGGCGTC 1260

CTGGCCAGCG CCCACCGCCC CCAGGGCCCG GCCGACGCCT GGCGCGCCGC GGTGCTGATC 1320

TACGCGAGCG ACGACACCCG CGCCCACCCC AACCGCAGCG TCGCGGTGAC CCTGCGGCTG 1380

CGCGGGGTGC CCCCCGGCCC GGGCCTGGTC TACGTCACGC GCTACCTGGA CAACGGGCTC 1440

TGCAGCCCCG ACGGCGAGTG GCGGCGCCTG GGCCGGCCCG TCTTCCCCAC GGCAGAGCAG 1500

-continued

```
TTCCGGCGCA TGCGCGCGGC TGAGGACCCG GTGGCCGCGG CGCCCCGCCC CTTACCCGCC   1560

GGCGGCCGCC TGACCCTGCG CCCCGCGCTG CGGCTGCCGT CGCTTTTGCT GGTGCACGTG   1620

TGTGCGCGCC CCGAGAAGCC GCCCGGGCAG GTCACGCGGC TCCGCGCCCT GCCCCTGACC   1680

CAAGGGCAGC TGGTTCTGGT CTGGTCGGAT GAACACGTGG GCTCCAAGTG CCTGTGGACA   1740

TACGAGATCC AGTTCTCTCA GGACGGTAAG GCGTACACCC CGGTCAGCAG GAAGCCATCG   1800

ACCTTCAACC TCTTTGTGTT CAGCCCAGAC ACAGGTGCTG TCTCTGGCTC CTACCGAGTT   1860

CGAGCCCTGG ACTACTGGGC CCGACCAGGC CCCTTCTCGG ACCCTGTGCC GTACCTGGAG   1920

GTCCCTGTGC CAAGAGGGCC CCCATCCCCG GGCAATCCAT GAGCCTGTGC TGAGCCCCAG   1980

TGGGTTGCAC CTCCACCGGC AGTCAGCGAG CTGGGGCTGC ACTGTGCCCA TGCTGCCCTC   2040

CCATCACCCC CTTTGCAATA TATTTTT                                       2067
```

(2) INFORMATION FOR SEQ ID NO:9:

(i) SEQUENCE CHARACTERISTICS:
(A) LENGTH: 653 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:9:

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Thr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
```

-continued 245 250 255

Asp Tyr Ile Ser Leu His Arg Lys Gly Ala Arg Ser Ser Ile Ser Ile
260 265 270

Leu Glu Gln Glu Lys Val Val Ala Gln Glu Ile Arg Gln Leu Phe Pro
275 280 285

Lys Phe Ala Asp Thr Pro Ile Tyr Asn Asp Glu Ala Asp Pro Leu Val
290 295 300

Gly Trp Ser Leu Pro Gln Pro Trp Arg Ala Asp Val Thr Tyr Ala Ala
305 310 315 320

Met Val Val Lys Val Ile Ala Gln His Gln Asn Leu Leu Leu Ala Asn
325 330 335

Thr Thr Ser Ala Phe Pro Tyr Ala Leu Leu Ser Asn Asp Asn Ala Phe
340 345 350

Leu Ser Tyr His Pro His Pro Phe Ala Gln Arg Thr Leu Thr Ala Arg
355 360 365

Phe Gln Val Asn Asn Thr Arg Pro Pro His Val Gln Leu Leu Arg Lys
370 375 380

Pro Val Leu Thr Ala Met Gly Leu Leu Ala Leu Leu Asp Glu Glu Gln
385 390 395 400

Leu Trp Ala Glu Val Ser Gln Ala Gly Thr Val Leu Asp Ser Asn His
405 410 415

Thr Val Gly Val Leu Ala Ser Ala His Arg Pro Gln Gly Pro Ala Asp
420 425 430

Ala Trp Arg Ala Ala Val Leu Ile Tyr Ala Ser Asp Asp Thr Arg Ala
435 440 445

His Pro Asn Arg Ser Val Ala Val Thr Leu Arg Leu Arg Gly Val Pro
450 455 460

Pro Gly Pro Gly Leu Val Tyr Val Thr Arg Tyr Leu Asp Asn Gly Leu
465 470 475 480

Cys Ser Pro Asp Gly Glu Trp Arg Arg Leu Gly Arg Pro Val Phe Pro
485 490 495

Thr Ala Glu Gln Phe Arg Arg Met Arg Ala Ala Glu Asp Pro Val Ala
500 505 510

Ala Ala Pro Arg Pro Leu Pro Ala Gly Gly Arg Leu Thr Leu Arg Pro
515 520 525

Ala Leu Arg Leu Pro Ser Leu Leu Leu Val His Val Cys Ala Arg Pro
530 535 540

Glu Lys Pro Pro Gly Gln Val Thr Arg Leu Arg Ala Leu Pro Leu Thr
545 550 555 560

Gln Gly Gln Leu Val Leu Val Trp Ser Asp Glu His Val Gly Ser Lys
565 570 575

Cys Leu Trp Thr Tyr Glu Ile Gln Phe Ser Gln Asp Gly Lys Ala Tyr
580 585 590

Thr Pro Val Ser Arg Lys Pro Ser Thr Phe Asn Leu Phe Val Phe Ser
595 600 605

Pro Asp Thr Gly Ala Val Ser Gly Ser Tyr Arg Val Arg Ala Leu Asp
610 615 620

Tyr Trp Ala Arg Pro Gly Pro Phe Ser Asp Pro Val Pro Tyr Leu Glu
625 630 635 640

Val Pro Val Pro Arg Gly Pro Pro Ser Pro Gly Asn Pro
645 650

(2) INFORMATION FOR SEQ ID NO:10:

-continued (i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:10:

```
Asp Tyr Lys Asp Asp Asp Asp Lys
1               5
```

(2) INFORMATION FOR SEQ ID NO:11:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: other nucleic acid
(A) DESCRIPTION: /desc = "PCR primer"

(xi) SEQUENCE DESCRIPTION: SEQ ID NO:11:

```
GCCTATGCTG AGCACAAGTT ACAG                                          24
```

(2) INFORMATION FOR SEQ ID NO:12:

(i) SEQUENCE CHARACTERISTICS:
(A) LENGTH: 34 base pairs
(B) TYPE: nucleic acid
(C) STRANDEDNESS: unknown
(D) TOPOLOGY: unknown (ii) MOLECULE TYPE: other nucleic acid
(A) DESCRIPTION: /desc = "Complementary sequence of a PCR primer"

(xi) SEQUENCE DESCRIPTION: SEQ ID NO:12:

```
TCCCTTGAGC TCGTCACTGG CGACGCCACA GGTA                               34
```

(2) INFORMATION FOR SEQ ID NO:13:

(i) SEQUENCE CHARACTERISTICS:
(A) LENGTH: 48 base pairs
(B) TYPE: nucleic acid
(C) STRANDEDNESS: unknown
(D) TOPOLOGY: unknown (ii) MOLECULE TYPE: other nucleic acid (xi) SEQUENCE DESCRIPTION: SEQ ID NO:13:

```
CAGAATTCGG ACTACAAGGA CGACGATGAC AAGTAGGAGC TCGAATTC                48
```

(2) INFORMATION FOR SEQ ID NO:14:

(i) SEQUENCE CHARACTERISTICS:
(A) LENGTH: 10 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:14:

```
Asn Ser Asp Tyr Lys Asp Asp Asp Asp Lys
1               5                   10
```

(2) INFORMATION FOR SEQ ID NO:15:

-continued

```
    (i) SEQUENCE CHARACTERISTICS:
         (A) LENGTH: 4 amino acids
         (B) TYPE: amino acid
         (C) STRANDEDNESS: single
         (D) TOPOLOGY: unknown

   (ii) MOLECULE TYPE: peptide

   (xi) SEQUENCE DESCRIPTION: SEQ ID NO:15:

Lys Asp Glu Leu
```

PRODUCTION OF LYSOSOMAL ENZYMES IN PLANT-BASED EXPRESSION SYSTEMS

This application is a continuation-in-part of provisional application Ser. No. 60/003,737, filed Sept. 14, 1995, the disclosure of which is incorporated herein in its entirety.

This invention was made with United States government support under grant nos. NS32369 and DK48570 awarded by the National Institutes of Health. The government has certain rights in the invention.

TABLE OF CONTENTS

1. FIELD OF THE INVENTION 1
2. BACKGROUND OF THE INVENTION 1
  2.1. LYSOSOMAL STORAGE DISEASES 1
    2.1.1. GAUCHER DISEASE AND TREATMENT 2
    2.1.2. HURLER SYNDROME AND TREATMENT 4
  2.2. BIOSYNTHESIS OF LYSOSOMAL ENZYMES 5
  2.3. MAMMALIAN LYSOSOMES VERSUS PLANT VACUOLES 8
3. SUMMARY OF THE INVENTION 9
4. BRIEF DESCRIPTION OF THE FIGURES 10
5. DETAILED DESCRIPTION OF THE INVENTION 16
  5.1. GENES OR CODING SEQUENCES FOR ENZYMES INVOLVED IN LYSOSOMAL STORAGE DISEASES 19
  5.2. TRANSFORMATION VECTORS TO DIRECT THE EXPRESSION OF LYSOSOMAL ENZYME CODING SEQUENCE 21
    5.2.1. LYSOSOMAL ENZYME EXPRESSION CONSTRUCTS 21
    5.2.2. PLANT TRANSFORMATION VECTORS 24
  5.3. TRANSFORMATION/TRANSFECTION OF PLANTS 25
  5.4. IDENTIFICATION AND PURIFICATION OF THE LYSOSOMAL ENZYME GENE PRODUCT 28
    5.4.1. PRODUCTION AND PURIFICATION OF THE LYSOSOMAL ENZYME GENE PRODUCT 29
    5.4.2. PROTEOLYTIC PROCESSING OF THE SIGNAL PEPTIDE 31
    5.4.3. N-LINKED GLYCOSYLATION IN PLANTS VERSUS ANIMALS 31
  5.5. CLONAL PROPAGATION AND BREEDING OF TRANSGENIC PLANTS 32
  5.6. METHODS FOR THERAPEUTIC USE OF LYSOSOMAL ENZYMES 33
6. EXAMPLE 1: PRODUCTION AND ISOLATION OF RECOMBINANT MODIFIED hGC FROM TRANSGENIC TOBACCO PLANTS 36
  6.1. CONSTRUCTION OF A MODIFIED hGC EXPRESSION CONSTRUCT AND INSERTION INTO A PLANT TRANSFORMATION VECTOR 36
    6.1.1. PROMOTER:hGC EXPRESSION CONSTRUCT 36
    6.1.2. GENERATION OF A MeGA:hGC:FLAG™ CONSTRUCT 37
    6.1.3. INSERTION OF THE MeGA:hGC:FLAG™ CONSTRUCT INTO A PLANT TRANSFORMATION VECTOR 38
  6.2. INTRODUCTION OF THE MeGA:hGC:FLAG™ EXPRESSION CONSTRUCT INTO TOBACCO AND ASSESSMENT OF hGC:FLAG™ EXPRESSION 39
    6.2.1. GENERATION OF TRANSGENIC TOBACCO PLANTS CONTAINING THE MeGA:hGC:FLAG™ CONSTRUCT 39
    6.2.2. SOUTHERN ANALYSIS OF MeGA:hGC:FLAG™ INSERTIONS IN TRANSGENIC PLANTS 40
    6.2.3. NORTHERN ANALYSIS OF TRANSCRIPTIONAL ACTIVATION OF THE MeGA:hGC:FLAG™ TRANSGENE 40
    6.2.4. IMMUNODETECTION OF THE hGC:FLAG™ PROTEIN IN TRANSGENIC PLANT EXTRACTS 41
    6.2.5. ENZYMATIC ACTIVITY IN TOBACCO EXTRACTS 42
7. EXAMPLE 2: PRODUCTION AND PURIFICATION OF IDUA IN TRANSGENIC TOBACCO PLANTS 47
  7.1. CONSTRUCTION OF A PLANT TRANSFORMATION VECTOR CONTAINING AN IDUA EXPRESSION CONSTRUCT 47
    7.1.1. IDUA EXPRESSION CONSTRUCT 47
    7.1.2. IDUA EXPRESSION/TRANSFORMATION VECTORS 49
  7.2. GENERATION OF TRANSGENIC TOBACCO CONTAINING THE IDUA CONSTRUCTS 50
  7.3. SOUTHERN CHARACTERIZATION OF TRANSGENIC PLANTS 51
  7.4. CHARACTERIZATION OF IDUA EXPRESSION IN TRANSGENIC PLANTS 51
    7.4.1. IMMUNO-DETECTION OF IDUA PROTEIN IN PLANT EXTRACT 51
    7.4.2. NORTHERN ANALYSIS SHOWS ACTIVATION OF THE MEGA:IDUA TRANSGENE 53
    7.4.3. WESTERN ANALYSIS OF HUMAN IDUA LOCALIZED TO TOBACCO 53
    7.4.4. IDUA SYNTHESIZED IN TRANSGENIC TOBACCO IS SECRETED 54
    7.4.5. THE TOBACCO-SYNTHESIZED IDUA IS ENZYMATICALLY ACTIVE 54
    7.4.6. SECRETION AND RECOVERY OF TOBACCO-SYNTHESIZED RECOMBINANT IDUA 55
    7.4.7. PURIFICATION AND YIELD OF IDUA FROM TRANSGENIC TOBACCO 56
8. EXAMPLE 3: PRODUCTION OF TRANSGENIC TOBACCO PLANTS CONTAINING AN UNMODIFIED hGC EXPRESSION CONSTRUCT 57
9. DEPOSIT OF BIOLOGICAL MATERIALS 58

1. FIELD OF THE INVENTION

The present invention relates to the production of human and animal lysosomal enzymes in plants comprising expressing the genetic coding sequence of a human or animal lysosomal enzyme in a plant expression system. The plant expression system provides for post-translational modification and processing to produce recombinant protein having enzymatic activity.

The invention is demonstrated herein by working examples in which transgenic tobacco plants produce a modified human glucocerebrosidase (hGC) and a human α-L-iduronidase (IDUA), both of which are enzymatically active.

The recombinant lysosomal enzymes produced in accordance with the invention may be used for a variety of purposes including but not limited to enzyme replacement therapy for the therapeutic treatment of lysosomal storage diseases, research for development of new approaches to medical treatment of lysosomal storage diseases, and industrial processes involving enzymatic substrate hydrolysis.

2. BACKGROUND OF THE INVENTION

2.1. LYSOSOMAL STORAGE DISEASES

Lysosomes, which are present in all animal cells, are acidic cytoplasmic organelles that contain an assortment of hydrolytic enzymes. These enzymes function in the degradation of internalized and endogenous macromolecular substrates. When there is a lysosomal enzyme deficiency, the deficient enzyme's undegraded substrates gradually accumulate within the lysosomes causing a progressive increase in the size and number of these organelles within the cell. This accumulation within the cell eventually leads to malfunction of the organ and to the gross pathology of a lysosomal storage disease, with the particular disease depending on the particular enzyme deficiency. More than thirty distinct, inherited lysosomal storage diseases have been characterized in humans.

A few examples of lysosomal storage diseases (and their associated deficient enzymes) include Fabry disease (α-galactosidase), Farber disease (ceramidase), Gaucher disease (glucocerebrosidase), $G_{ml}$ gangliosidosis (β-galactosidase), Tay-Sachs disease (β-hexosaminidase), Niemann-Pick disease (sphingomyelinase), Schindler disease (α-N-acetylgalactosaminidase), Hunter syndrome (iduronate-2-sulfatase), Sly syndrome (β-glucuronidase), Hurler and Hurler/Scheie syndromes (iduronidase), and I-Cell/San Filipo syndrome (mannose 6-phosphate transporter).

One proven treatment for lysosomal storage diseases is enzyme replacement therapy in which an active form of the enzyme is administered directly to the patient. However, abundant, inexpensive and safe supplies of therapeutic lysosomal enzymes are not commercially available for the treatment of any of the lysosomal storage diseases.

2.1.1. GAUCHER DISEASE AND TREATMENT

Gaucher disease is the most common lysosomal storage disease in humans, with the highest frequency encountered in the Ashkenazi Jewish population. About 5,000 to 10,000 people in the United States are afflicted with this disease (Grabowski, 1993, Adv. Hum. Genet. 21:377–441). Gaucher disease results from a deficiency in glucocerebrosidase (hGC; glucosylceramidase; acid β-glucosidase; EC 3.2.1.45). This deficiency leads to an accumulation of the enzyme's substrate, glucocerebroside, in reticuloendothelial cells of the bone marrow, spleen and liver, resulting in significant skeletal complications such as bone marrow expansion and bone deterioration, and also hypersplenism, hepatomegaly, thrombocytopenia, anemia and lung complications (Grabowski, 1993, supra; Lee, 1982, Prog. Clin. Biol. Res. 95:177–217; Brady et al., 1965, Biochem. Biophys. Res. Comm. 18:221–225).

hGC replacement therapy has revolutionized the medical care and management of Gaucher disease, leading to significant improvement in the quality of life of many Gaucher patients (Pastores et al., 1993, Blood 82:408–416; Fallet et al., 1992, Pediatr. Res. 31:496–502). Studies have shown that regular, intravenous administration of specifically modified hGC (Ceredase™, Genzyme Corp.) can result in dramatic improvements and even reversals in the hepatic, splenic and hematologic manifestations of the disease (Pastores et al., 1993, supra; Fallet: et al., 1992, supra; Figueroa et al., 1992, N. Eng. J. Med 327:1632–1636; Barton et al., 1991, N. Eng. J. Med. 324:1464–1470; Beutler et al., 1991, Blood 78:1183–1189). Improvements in associated skeletal and lung complications are possible, but require larger doses of enzyme over longer periods of time.

Despite the benefits of hGC replacement therapy, the source and high cost of the enzyme seriously restricts its availability. Until recently, the only commercial source of purified hGC has been from pooled human placentae, where ten to twenty kilograms (kg) of placentae yield only 1 milligram (mg) of enzyme. From five hundred to two thousand kilograms of placenta (equivalent to 2,000–8,000 placentae) are required to treat each patient every two weeks. Current costs for HGC replacement therapy range from $55 to $220/kg patient body weight every two weeks, or from $70,000 to $300,000/year for a 50 kg patient. Since the need for therapy essentially lasts for the duration of a patient's life, costs for the enzyme alone may exceed $15, 000,000 during 30 to 70 years of therapy.

A second major problem associated with treating Gaucher patients with glucocerebrosidase isolated from human tissue (and perhaps even from other animal tissues) is the risk of exposing patients to infectious agents which may be present in the pooled placentae, e.g., human immuno-deficiency virus (HIV), hepatitis viruses, and others.

Accordingly, a new source of hGC is needed to effectively reduce the cost of treatment and to eliminate the risk of exposing Gaucher patients to infectious agents.

2.1.2. HURLER SYNDROME AND TREATMENT

Hurler syndrome is the most common of the group of human lysosomal storage disorders known as the mucopolysaccharidoses (MPS) involving an inability to degrade dermatan sulfate and heparan sulfate. Hurler patients are deficient in the lysosomal enzyme, α-L-iduronidase (IDUA), and the resulting accumulation of glucosaminoglycans in the lysosomes of affected cells leads to a variety of clinical manifestations (Neufeld & Ashwell, 1980, *The Biochemistry of Glycoproteins and Proteoglycans*, ed. W. J. Lennarz, Plenum Press, N.Y.; pp. 241–266) including developmental delay, enlargement of the liver and spleen, skeletal abnormalities, mental retardation, coarsened facial features, corneal clouding, and respiratory and cardiovascular involvement. Hurler/Scheie syndrome (MPS I H/S) and Scheie syndrome (MPS IS) represent less severe forms of the disorder but also involve deficiencies in IDUA. Molecular studies on the genes and cDNAs of MPS I patients has led to an emerging understanding of genotype and clinical phenotype (Scott et al., 1990, Am. J. Hum. Genet. 47:802–807). In addition, both a canine and feline form of MPS I have been characterized (Haskins et al., 1979, Pediat. Res. 13:1294–1297; Haskins and Kakkis, 1995, Am. J. Hum. Genet. 57:A39 Abstr. 194; Shull et al., 1994, Proc. Natl. Acad. Sci. USA, 91:12937–12941) providing an effective in vivo model for testing therapeutic approaches.

The efficacy of enzyme replacement in the canine model of Hurler syndrome using human IDUA generated in CHO cells was recently reported (Kakkis et al., 1995, Am. J. Hum. Genet. 57:A39 (Abstr.); Shull et al., 1994, supra). Weekly doses of approximately 1 mg administered over a period of 3 months resulted in normal levels of the enzyme in liver and spleen, lower but significant levels in kidney and Lungs and very low levels in brain, heart, cartilage and cornea (Shull et al., 1994, supra. Tissue examinations showed normalization of lysosomal storage in the liver, spleen and kidney, but no improvement in heart, brain and corneal tissues. One dog was maintained on treatment for 13 months and was clearly more active with improvement in skeletal deformities, joint stiffness, corneal clouding and weight gain (Kakkis et al., 1995, supra. A single higher-dose experiment was quite promising and showed detectable IDUA activity in the brain and cartilage in addition to tissues which previously showed activity at the lower does. Additional higher-dose experiments and trials involving longer administration are currently limited by availability of recombinant enzyme. These experiments underscore the potential of replacement therapy for Hurler patients and the severe constraints on both canine and human trials due to limitations in recombinant enzyme production using current technologies.

2.2. BIOSYNTHESIS OF LYSOSOMAL ENZYMES

Soluble lysosomal enzymes share initial steps of biosynthesis with secretory proteins, i.e., synthesis on the ribosome, binding of the N-terminal signal peptide to the surface of the rough endoplasmic reticulum (ER), transport into the lumen of the ER where the signal peptide is cleaved, and addition of oligosaccharides to specific asparagine residues (N-linked), followed by further modifications of the nascent protein in the Golgi apparatus (von Figura and Hasilik, 1986, Annu. Rev. Biochem. 55:167–193). The N-linked oligosaccharides can be complex, diverse and heterogeneous, and may contain high-mannose residues. The proteins undergo further processing in a post-ER, pre-Golgi compartment and in the cis-Golgi to form either an N-linked mannose 6-phosphate (M-6-P) oligosaccharide-dependent or N-linked M-6-P oligosaccharide-independent recognition signal for lysosomal localized enzymes (Kornfeld & Mellman, 1989, Ann. Rev. Cell Biol., 5:483–525; Kaplan et al., 1977, Proc. Natl. Acad. Sci. USA 74:2026). The presence of the M-6-P recognition signal results in the binding of the enzyme to M-6-P receptors (MPR). These bound enzymes remain in the cell, are eventually packaged into lysosomes, and are thus segregated from proteins targeted for secretion or to the plasma membrane.

Although many lysosomal enzymes are soluble and are transported to lysosomes by MPRs, integral membrane and membrane-associated proteins (notably hGC) are targeted and transported to lysosomes independent of the M-6-P/MPR system (Kornfeld & Mellman, 1989, Erickson et al., 1985). hGC does not become soluble after translation, but instead becomes associated with the lysosomal membrane by means which have not been elucidated (von Figura & Hasilik, 1986, Annu. Rev. Biochem. 55:167–193; Kornfeld and Mellman, 1989, Annu. Rev. Cell Biol. 5:483–525).

hGC is synthesized as a single polypeptide (58 kDa) with a signal sequence (2 kDa) at the amino terminus. The signal sequence is co-translationally cleaved and the enzyme is glycosylated with a heterogeneous group of both complex and high-mannose oligosaccharides to form a precursor. The glycans are predominately involved in protein conformation. The "high mannose" precursor, which has a molecular weight of 63 Kda, is post-translationally processed in the Golgi to a 66 Kda intermediate, which is then further modified in the lysosome to the mature enzyme having a molecular weight of 59 Kda (Jonsson et al., 1987, Eur. J. Biochem. 164:171; Erickson et al., 1985, J. Biol. Chem., 260:14319).

The mature hGC polypeptide is composed of 497 amino acids and contains five N-glycosylation amino acid consensus sequences (Asn-X-Ser/Thr). Four of these sites are normally glycosylated. Glycosylation of the first site is essential for the production of active protein. Both high-mannose and complex oligosaccharide chains have been identified (Berg-Fussman et al., 1993, J. Biol. Chem. 268:14861–14866). hGC from placenta contains 7% carbohydrate, 20% of which is of the high-mannose type (Grace & Grabowski, 1990, Biochem. Biophys. Res. Comm. 168:771–777). Treatment of placental hGC with neuraminidase (yielding an asialo enzyme) results in increased clearance and uptake rates by rat liver cells with a concomitant increase in hepatic enzymatic activity (Furbish et al., 1981, Biochim. Biophys. Acta 673:425–434). This glycan-modified placental hGC is currently used as a therapeutic agent in the treatment of Gaucher's disease. Biochemical and site-directed mutagenesis studies have provided an initial map of regions and residues important to folding, activator interaction, and active site location (Grace et al., 1994, J. Biol. Chem. 269:2283–2291).

The complete complementary DNA (cDNA) sequence for hGC has been published (Tsuji et al., 1986, J. Biol. Chem. 261:50–53; Sorge et al., 1985, Proc. Natl. Acad. Sci. USA 82:7289–7293), and *E. coil* containing the hGC cDNA sequence cloned from fibroblast cells, as described (Sorge et al., 1985, supra), is available from the American Type Culture Collection (ATCC) (Accession No. 65696).

Recombinant methodologies have the potential to provide a safer and less expensive source of lysosomal enzymes for replacement therapy. However, production of active enzymes, e.g., hGC, in a heterologous system requires correct targeting to the ER, and appropriate N-linked glycosylation at levels or efficiencies that avoid ER-based degradation or aggregation. Since mature lysosomal enzymes must be glycosylated to be active, bacterial systems cannot be used. For example, hGC expressed in *E. coli* is enzymatically inactive (Grace & Grabowski, 1990, supra).

Active monomers of hGC have been purified from insect cells (Sf9 cells) and Chinese hamster ovary (CHO) cells infected or transfected, respectively, with hGC cDNA (Grace & Grabowski, 1990, supra; Grabowski et al., 1989, Enzyme 41:131–142). A method for producing recombinant hGC in CHO cell cultures and in insect cell cultures was recently disclosed in U.S. Pat. No. 5,236,838. Recombinant hGC produced in these heterologous systems had an apparent molecular weight ranging from 64 to 73 kDa and contained from 5 to 15% carbohydrate (Grace & Grabowski, 1990, supra; Grace et al., 1990, J. Biol. Chem. 265:6827–6835). These recombinant hGCs had kinetic properties identical to the natural enzyme isolated from human placentae, as based on analyses using a series of substrate and transition state analogues, negatively-charged lipid activators, protein activators (saposin C), and mechanism-based covalent inhibitors (Grace et al., 1994, supra; Berg-Fussman et al., 1993, supra; Grace et al., 1990, J. Biol. Chem. 265:6827–6835; Grabowski et al., 1989, supra). However, both insect cells and CHO cells retained most of the enzyme rather than secreting it into the medium, significantly increasing the difficulty and cost of harvesting the pure enzyme (Grabowski et al., 1989, supra).

Accordingly, a recombinant system is needed that can produce human or animal lysosomal enzymes in an active form at lower cost, and that will be appropriately targeted for ease of recovery.

2.3. MAMMALIAN LYSOSOMES VERSUS PLANT VACUOLES

Because plants are eukaryotes, plant expression systems have advantages over prokaryotic expression systems, particularly with respect to correct processing of eukaryotic gene products. However, unlike animal cells, plant cells do not possess lysosomes. Although the plant vacuole appears functionally analogous to the lysosome, plants do not contain MPRs (Chrispeels, 1991, Ann. Rev. Pl. Phys. Pl. Mol. Biol. 42:21–53; Chrispeels and Tague, 1991, Intl. Rev. Cytol. 125:1–45), and the mechanisms of vacuolar targeting can differ significantly from those of lysosomal targeting. For example, the predominant mechanism of vacuolar targeting in plants does not appear to be glycan-dependent, but appears to be based instead on C- or N-terminal peptide sequences (Gomez & Chrispeels, 1993, Plant Cell 5:1113–1124; Chrispeels & Raikhal, 1992, Cell 68:613–618;

Holwerda et al., 1992, Plant Cell 4:307–318; Neuhaus et al., 1991, Proc. Natl. Acad. Sci. USA 88:10362–10366; Chrispeels, 1991, supra; Chrispeels & Tague, 1991, supra; Holwerda et al., 1990, Plant Cell 2:1091–1106; Voelker et al., 1989, Plant Cell 1:95–104). As a result, plants have not been viewed as appropriate expression systems for lysosomal enzymes which must be appropriately processed to produce an active product.

3. SUMMARY OF THE INVENTION

The present invention relates to the production of human or animal lysosomal enzymes in transformed or transfected plants, plant cells or plant tissues, and involves constructing and expressing recombinant expression ccnstructs comprising lysosomal enzyme coding sequences in a plant expression system. The plant expression system provides appropriate co-translational and post-translational modifications of the nascent peptide required for processing, e.g., signal sequence cleavage, glycosylation, and sorting of the expression product so that an enzymatically active protein is produced. Using the methods described herein, recombinant lysosomal enzymes are produced in plant expression systems from which the recombinant lysosomal enzymes can be isolated and used for a variety of purposes. The present invention is exemplified by the genetic-engineering of transgenic tobacco plants with three lysosomal enzyme expression constructs. One construct comprises a nucleotide sequence encoding a modified human glucocerebrosidase (hGC), specifically a hGC fused at its C-terminal to the eight amino acid FLAG™ peptide (hGC:FLAG™). Another construct comprises nucleotide sequence encoding a human α-L-iduronidase (IDUA). The third construct zomprises a nucleotide sequence encoding a human glucocerebrosidase (hGC). Transgenic tobacco plants having the expression constructs produce lysosomal enzymes that are enzymatically active.

The plant expression systems and the recombinant lysosomal enzymes produced therewith have a varieta of uses, including but not limited to: (1) the production of enzymatically active lysosomal enzymes for the treatment of lysosomal storage diseases; (2) the production of altered or mutated proteins, enzymatically active or otherwise, to serve as precursors or substrates for further in vivo or in vitro processing to a specialized industrial form for research or therapeutic uses, such as to produce a more effective therapeutic enzyme; (3) the production of antibodies against lysosomal enzymes for medical diagnostic use; and (4) use in any commercial process that involves substrate hydrolysis.

4. BRIEF DESCRIPTION OF THE FIGURES

FIG. 1. hGC:FLAG™ cDNA plant expression construct and transformation vector. The MeGA:hGC:FLAG™ construct in a pBS intermediate vector is excised and inserted into the SstI site of the binary plant transformation vector pBIB-KAN to form plasmid CTPro1:hGC:FLAG. R and L represent T-DNA right and left borders, respectively, which precisely delineate the DNA inserted into the plant genome. NPTII=kanamycin selectable marker, FL=FLAG™ epitope (the nucleotide and amino acid sequences shown are SEQ ID NOS:13 & 14, respectively), pAnos=polyadenylation/terminator signal, Pnos=promoter sequence from *Agrobacterium tumefaciens* nopaline synthetase gene. PCR-amplification primers for hGC were: GC1 (5'TTG tcTAGaGTAAGCATCATGGCTGGC3') (SEQ ID NO:1); and GC4 (5'cac gaattCTGGCGACGCCACAGGTAGGTGTGA3') (SEQ ID NO:2); hGC-derived sequences are in upper case; restriction sites are underlined. Restriction enzymes: E, EcoRI; S, SstI; N, NotI; X, XbaI.

FIGS. 2A–E. Transformation and generation of tobacco plants carrying the MeGA:hGC:FLAG™ construct. FIG. 2A. Agrobacterium-mediated transformation of tobacco leaf discs. Leaf discs were inoculated with a cell suspension of *A. tumefaciens* strains carrying the plasmid CTPro1:hGC:FLAG. FIG. 2B. Development of shoots on selection media 22 days post-inoculation. FIG. 2C. Development of roots on rooting media 27 days post-inoculation. Use of rooting media containing kanamycin clearly differentiated between transgenic shoots which formed roots and "false positive" shoots which did not form roots on selective media. FIG. 2D. Transformed plants three weeks after transfer to soil. FIG. 2E. Transformed plant 10 weeks after transfer to soil.

Figure 3:
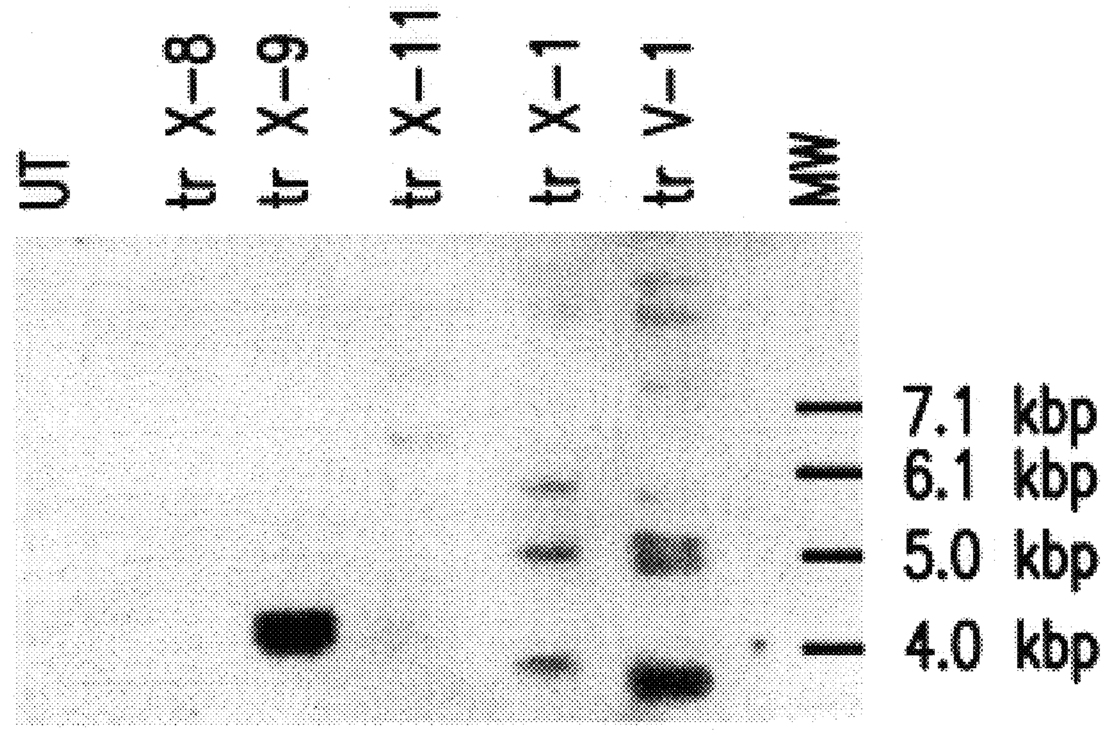

FIG. 3. Genomic Southern hybridization analysis of control and transgenic plants. Total genomic DNA was isolated from an untransformed control plant (UT) and independent transformants generated from *Nicotiana tabacum* cv. Xanthi (X-1, X-8, X-9, X-11) and cv. VA116 (V1). Five to 10 μg of total genomic DNA were digested with HindIII and resolved on a TBE agarose gel. The DNA was blotted to nitrocellulose membrane and probed with a $^{32}$P-labeled hGC:FLAG™ sequence from a gel-purified 1.7 kb HindIII fragment isolated from the pBS intermediate vector containing the MeGA:hGC:FLAG™ expression construct (see FIG. 1).

Figure 4:
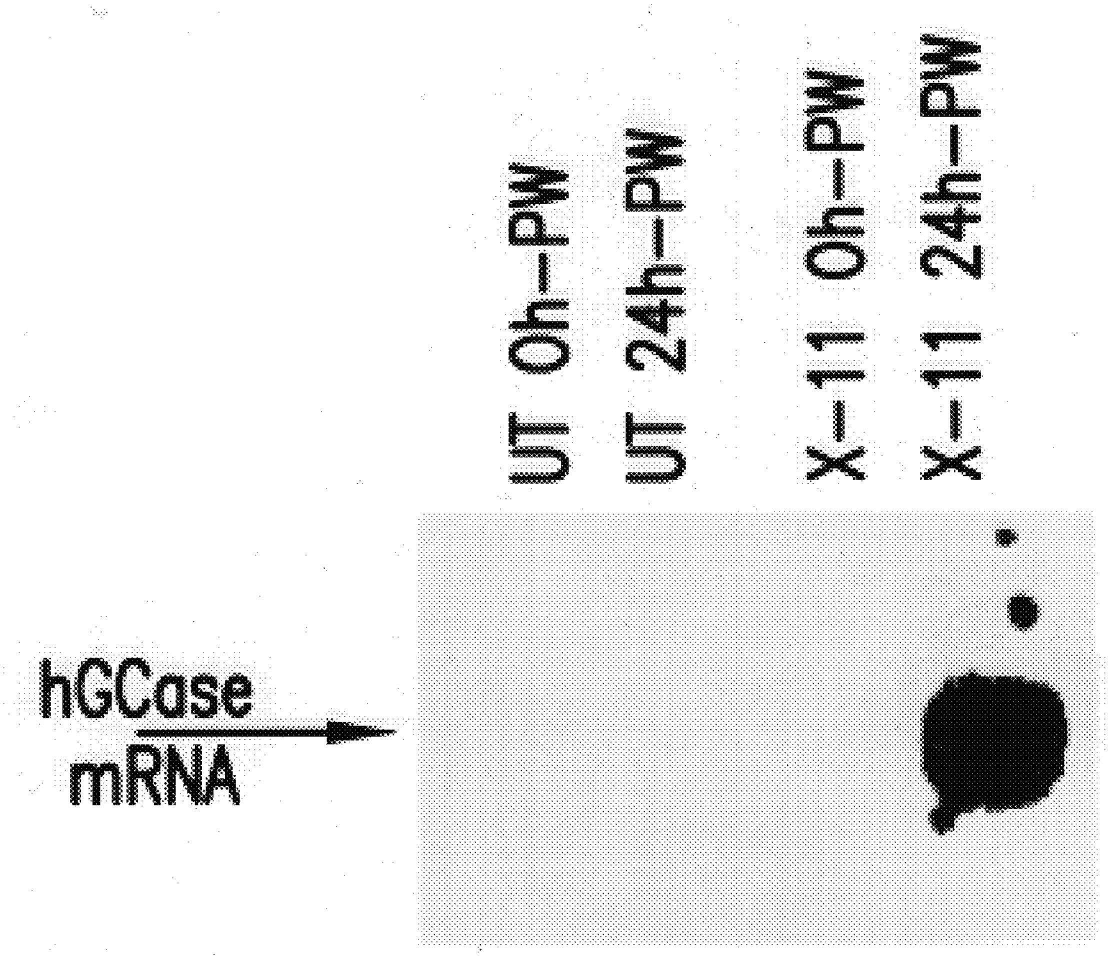

FIG. 4. Induction of hGC:FLAG™ mRNA levels in transgenic plants. Total RNA was isolated by standard guanidino-thiocyanate methods from UT and X-11 leaf tissue at 0 and 24 hr post-mechanical gene activation (MGA). Five μg of total RNA was glyoxylated, size-separated on a 1.2% agarose gel, transferred to NitroPure (MSI) filters and probed with a $^{32}$P-labeled hGC:FLAG™ gene sequence from a gel-purified 1.7 kb HindIII fragment isolated from the pBS intermediate vector shown in FIG. 1.

Figure 5A:
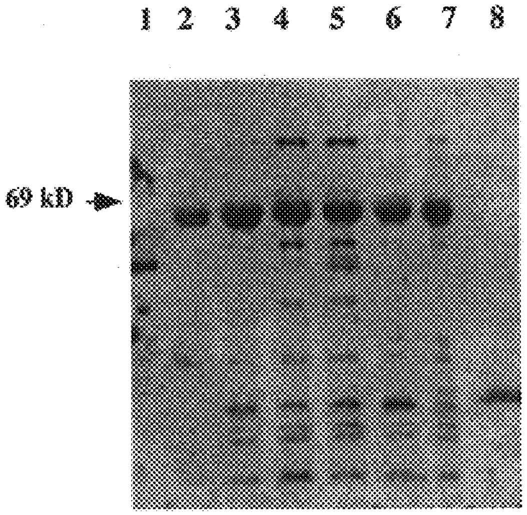
Figure 5B:
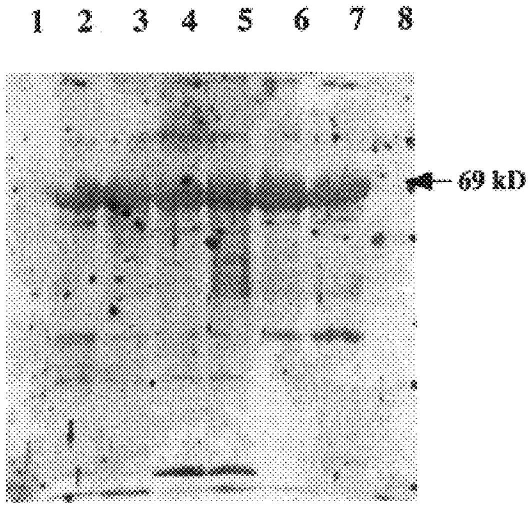

FIGS. 5A–B. Induction of hGC:FLAG™ fusion protein in transgenic tobacco plants as detected by Western analysis using anti-FLAG™ antibodies and anti-hGC antibodies. Leaf tissue from X-11 was induced by MGA at time 0 at room temperature, harvested at 2, 4, 8, 16, and 24 hrs, and frozen at −20° C. prior to extraction. hGC:FLAG™ was solubilized by grinding the tissue in a coffee bean grinder with dry ice and homogenized in 1% Triton X-100, 1% taurocholate, 25 mM sodium citrate pH 7.0, 4 mM β-mercaptoethanol, and 5 mM ethylenediaminetetraacetic acid (EDTA), followed by two cycles of freezing and thawing of the homogenate. Both protein concentration and enzyme activity of cell free extracts were determined. FIG. 5A. Ten μg of total soluble protein were analyzed by Western immunoblot using anti-FLAG™ antibodies. Lane 1, 24 ng of FLAG™-tagged control protein; lane 2, X-11 at time 0; lane 3, X-11 at 2 hr; lane 4, X-11 at 4 hrs; lane 5, X-11 at 8 hrs; lane 6, X-11 at 12 hrs; lane 7, X-11 at 24 hrs; lane 8, UT (control plant) at 12 hrs. FIG. 5B. Forty μg of total soluble protein were analyzed by Western immunoblot using anti-hGC antibodies. Lane 1, UT at time 0; lane 2, X-11 at time 0; lane 3, X-11 at 2 hrs; lane 4, X-11 at 4 hrs; lane 5, X-11 at 8 hrs; lane 6, X-11 at 12 hrs, lane 7, X-11 at 24 hrs; lane 8, UT at 8 hrs. The maximum level of hGC:FLAG™ expression was found between 8–12 hrs post-MGA.

Figure 6:
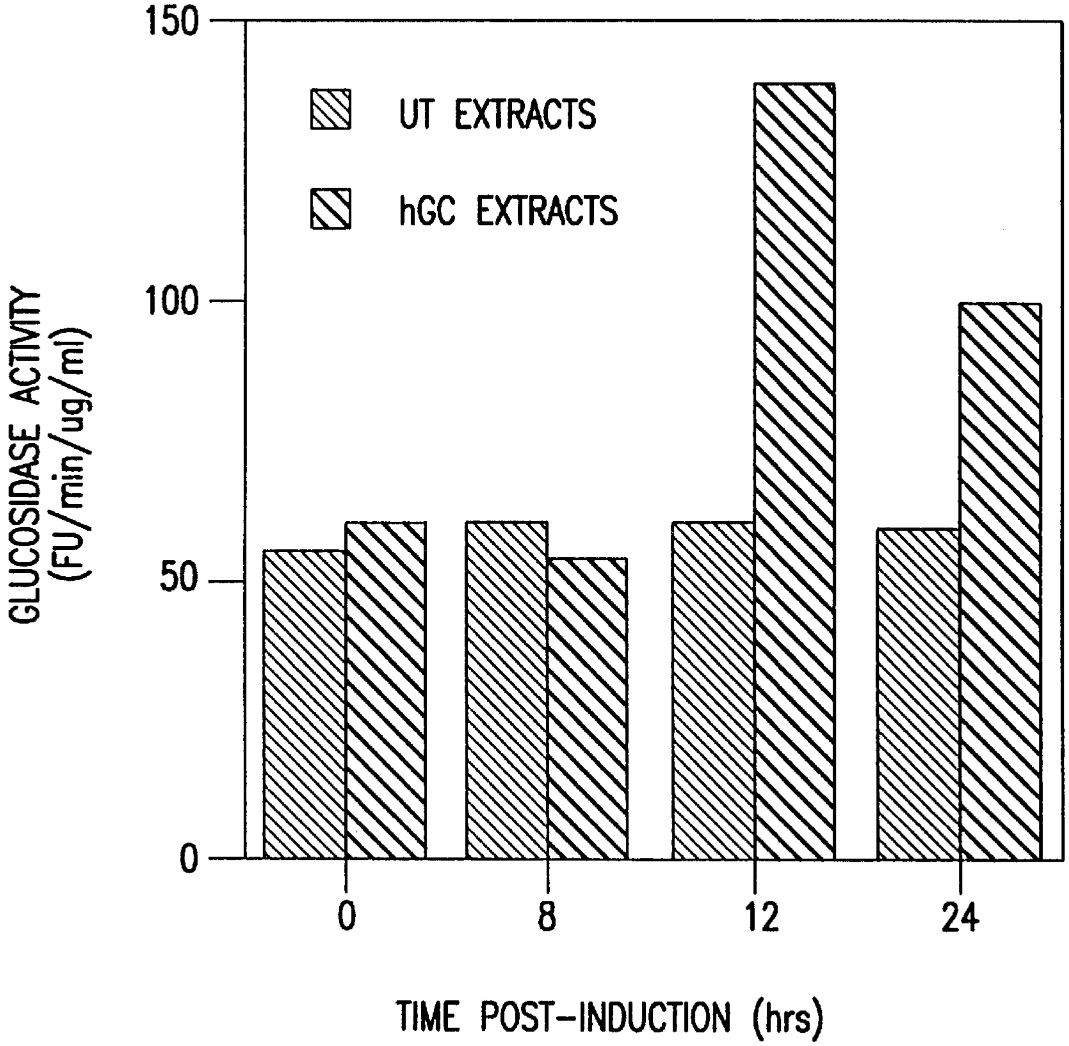

FIG. 6. Total β-glucosidase (endogenous plant β-glucosidase and hGC) activity post-MGA of X-11 leaf tissue. One-tenth μg of cell free extract was assayed for ability to convert the fluorometric substrate, 4-methylumbelliferyl-D-glucopyranoside (4MuGlc) to 4MU at 37° C., as measured in a fluorometer (Hoefer DyNA Quant-200, Hoefer, Pharmacia, Biotech. Inc.) with excitation at 365 nm and emission at 460 nm. FU=fluorometer units; Time=hrs post-inducti(on (i.e., wounding of tissue or MGA).

Figure 7A:
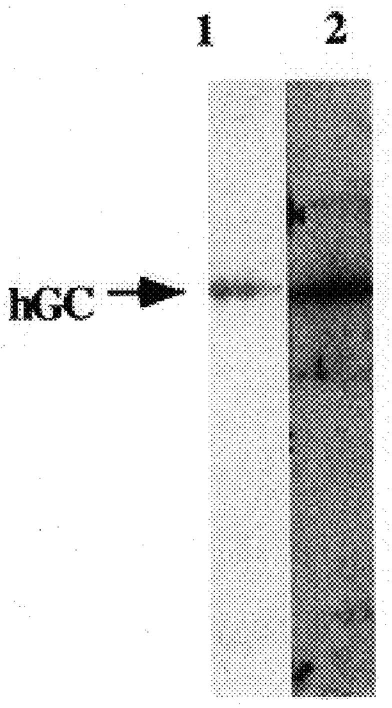
Figure 7B:
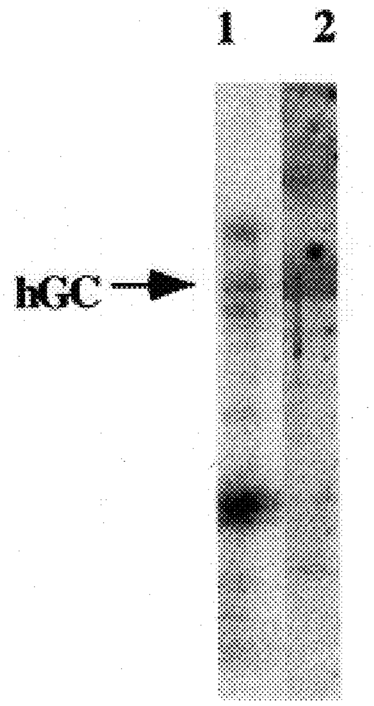

FIGS. 7A–B. Affinity purification of hGC:FLAG™ fusion protein. FIG. 7A. Commassie blue stained SDS-PAGE gel and Western analysis of FLAG™ affinity-purified hGC-:FLAG™. Lane 1, Coomassie blue stained SDS-PAGE gel of 0.1 μg FLAG™ affinity-purified hGC:FLAG™; Lane 2, Western analysis using anti-hGC antibodies on 0.1 μg FLAG™ affinity-purified hGC:FLAG™. FIG. 7B. Commassie blue stained SDS-PACE gel and Western analysis of ConA-affinity-purified hGC:FLAG™. Lane 1, Coomassie blue stained SDS-PAGE gel of 10 μg of ConA purified hGC:FLAG™; Lane 2, Western analysis of ConA purified hGC:™ using anti-FLAG™ antibodies. These results indicate that the ConA-purified hGC:FLAG™ protein is glycosylated.

Figure 8A:
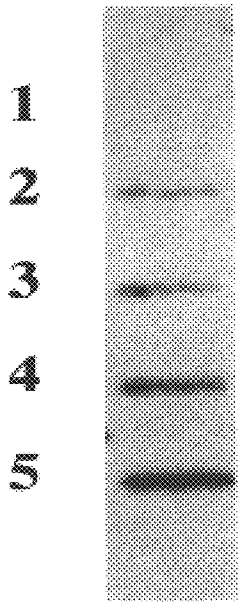
Figure 8B:
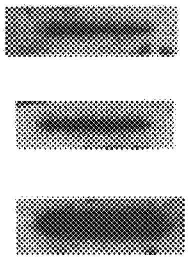
Figure 8C:
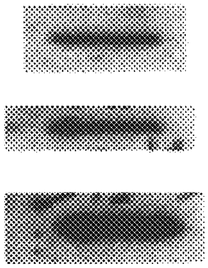

FIG. 8. Immuno-slot blot Western analysis using anti-FLAG™ antibodies on fractions from hGC:FLAG™ purification steps using plant tissue 12 hrs post-MGA. Lane A, FLAG™-tagged control protein: slot 1, 1 ng; slot 2, 6 ng; slot 3, 8 ng; slot 4, 18 ng; slot 5, 60 ng. Lane B, Fractions from isolation of hGC:FLAG™: slot 1, 0.5 μl/80,000 μl soluble protein from crude cell free extract; slot 2, 0.5 μl/80,000 μl soluble protein from 33% ammonium sulfate (AS) supernatant; slot 3, 2.5 μl/5,000 μl soluble protein from ConA affinity-purified hGC:FLAG™. Lane C: slot 1, 1 μl soluble protein from crude plant tissue extract; slot 2, 1 μl soluble protein from 33% AS supernatant; slot 3, 5 μl soluble protein from ConA affinity-purified hGC:FLAG™.

FIG. 9. Nucleotide sequence of hGC:FLAG™ construct (SEQ ID NO:3) which was cloned and expressed in tobacco strains X-11 and X-27. The upper case underlined letters at three positions represent changes to the sequence in GENBANK (ATCC bank cDNA sequence). The lower case letters represent additions to the hGC sequence, e.g., the FLAG™ epitope.

FIG. 10. Deduced amino acid sequence of hGC:FLAG™ fusion protein (SEQ ID NO:4). The upper case underlined letters at two positions represent changes to the original hGC amino acid sequence disclosed by E. Neufeld. Lower case letters represent additions to the hGC amino acid sequence. For example, dykddddk(SEQ ID NO:10)=the FLAG™ epitope.

FIG. 11. Sequence of 456 bases (SEQ ID NO:5) comprising the MeGA promoter.

Figure 12:
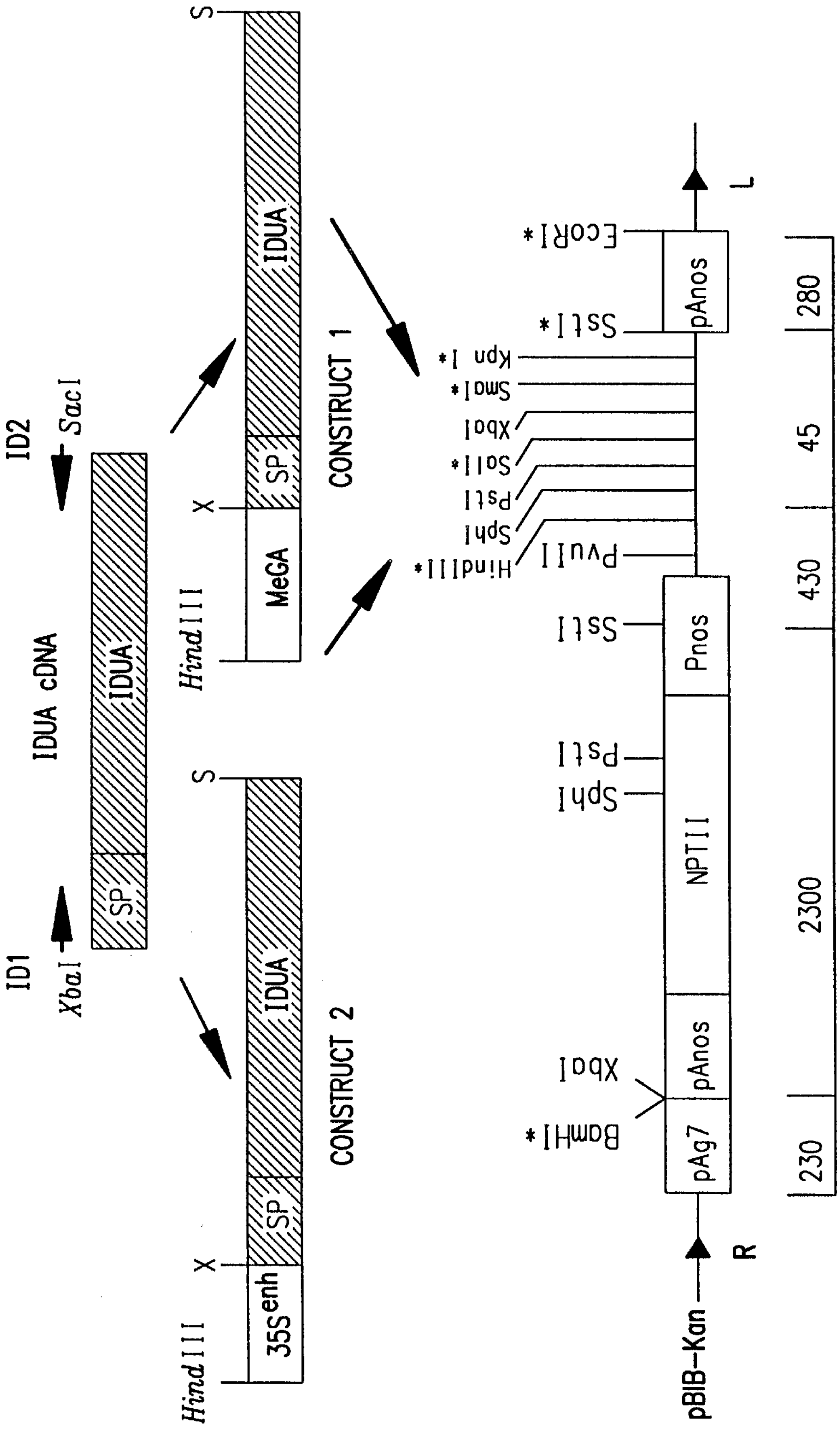

FIG. 12. IDUA expression vector construction sctrategy. MeGA:IDUA and $35S^{ENH}$:IDUA constructs were inserted into the HindIII/SacI site of the binary vector pBIB-KAN. R and L represent T-DNA right and left borders which precisely demarcate the DNA inserted into the plant genome, NPTII is the kanamycin selectable marker, pAnos is the polyadenylation/terminator signal and Pnos a promoter from *Agrobacterium tumefaciens* nopaline synthetase gene. PCR-primers for IDUA were: ID1, (5'-CTAG tctagaATGCGTCCCCTGCGCCCCCGCG) (SEQ ID NO:6) and ID2, (5'G gaattcgagctcTCATGGATTGCCCGGGGATG) (SEQ ID NO:7); IDUA sequences are capitalized, introduced restriction sites are underlined. SP, signal peptide; IDUA, human IDUA coding region; H, HindIII; S, SacI; X, XbaI.

FIGS. 13A–C. Transgenic tobacco expressing the MeGA:IDUA construct. FIG. 13A. Germination of first generation seeds on selective medium showing segregation of kanamycin resistant and sensitive seedlings. FIG. 13B. Young plants containing the MeGA:IDUA construct (right) and untransformed parent plants grown in parallel. FIG. 13C. Fully mature IDUA-expressing plants in the greenhouse.

Figure 14A:
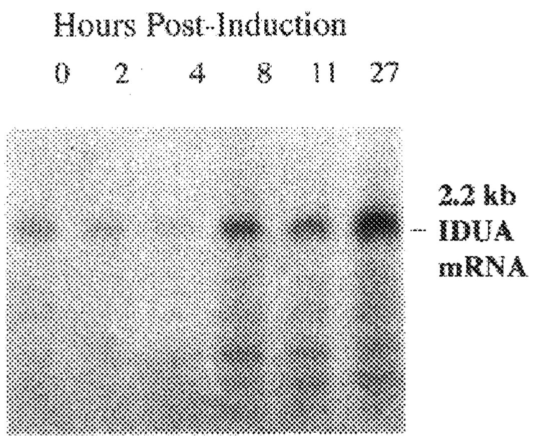
Figure 14B:
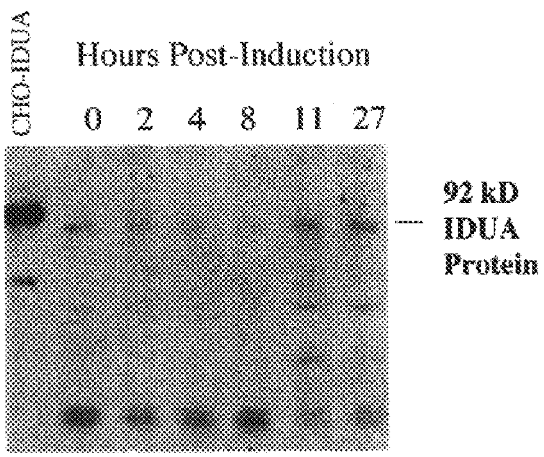

FIGS. 14A–B. Induction of IDUA transgene in tobacco leaf tissues. Leaf tissue from transgenic plant IDUA-9 was induced by excision into 1.5 mm strips and incubated at room temperature on moist paper towels in sealed plastic bag. Tissue was removed for analysis (stored at −80° C. for RNA, −20° C. for protein) at 0, 2, 4, 8, 11, and 27 hrs post-induction. FIG. 14A. Northern blot analysis of IDUA mRNA from transgenic tobacco plants. Fifteen μg of total RNA was run on glyoxal agarose gel, blotted onto nitrocellulose membrane, and hybridized with $^{32}$P-labeled IDUA cDNA. FIG. 14B. Western blot analysis of total soluble proteins (20 μg) from tobacco leaf extracts using antibodies to denatured IDUA synthesized in CHO cells. Control lane represents IDUA synthesized in CHO cells (98 kDa under our gel conditions). IDUA synthesized from transgenic tobacco has a molecular size of 92 kDa.

Figure 15A:
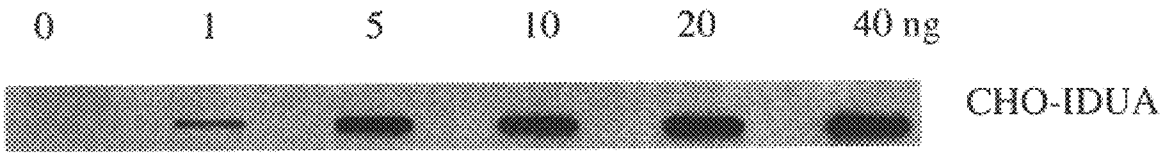
Figure 15B:
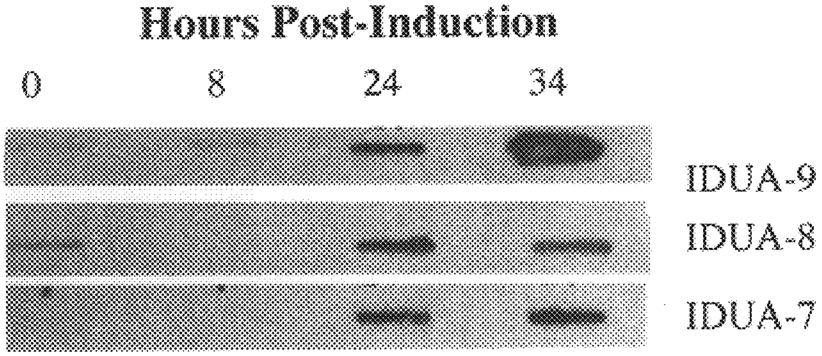

FIG. 15. Immunodetection of IDUA secreted by transgenic plants into the incubation buffer. Fifty μl of incubation buffer was boiled and slotted onto OPTITRAN membrane along with control IDUA synthesized in CHO cells. Antibodies to denatured IDUA synthesized in CHO cells were used to detect IDUA.

Figure 16A:
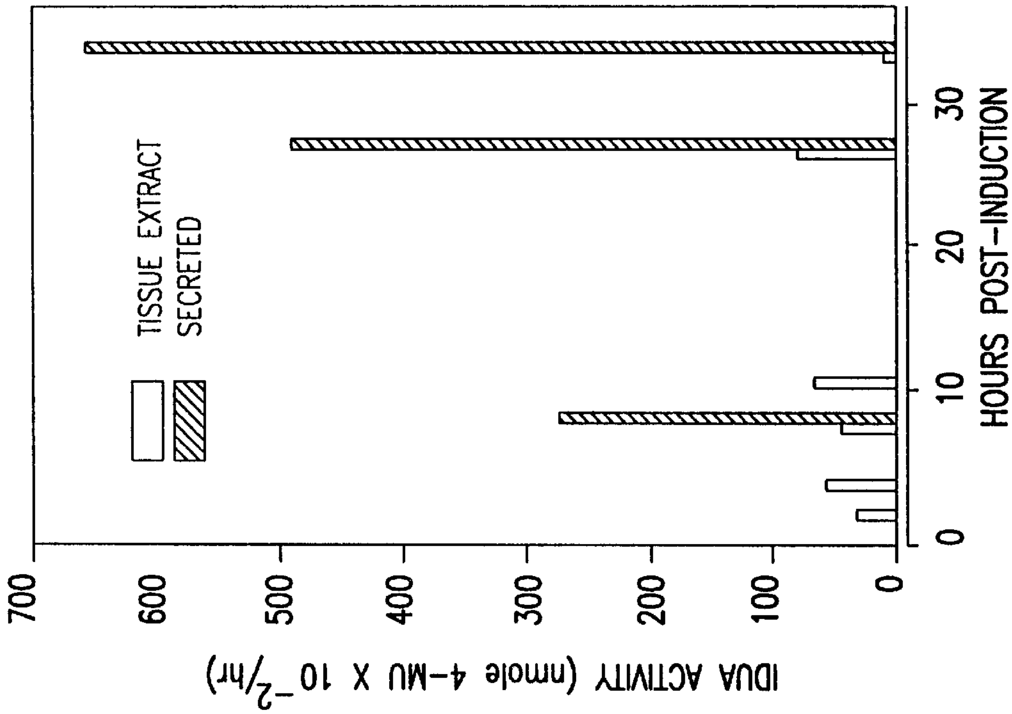
Figure 16B:
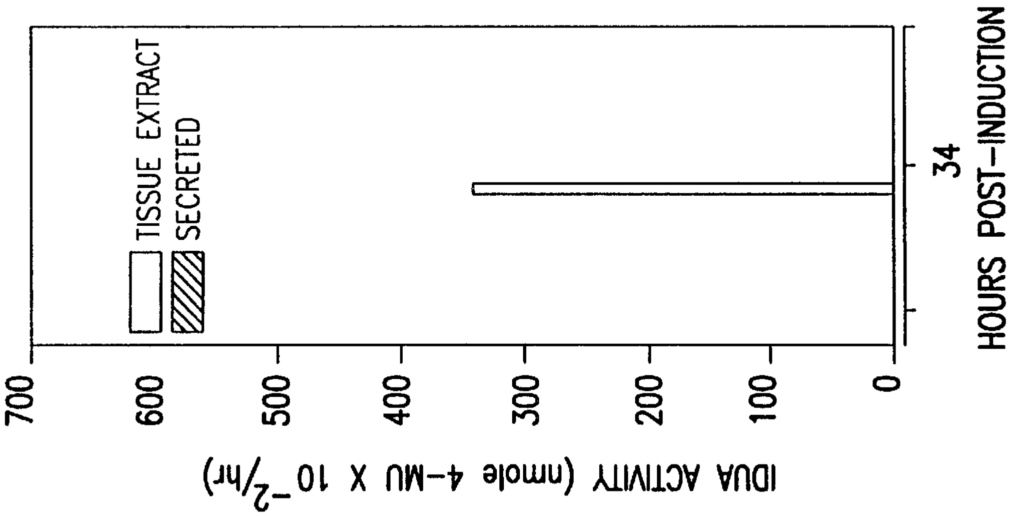

FIG. 16. IDUA activity in tissue extracts and incubation buffer from transgenic IDUA-9 plant tissue. Panel A: IDUA-9 plant tissue was induced and incubated in buffer, which was collected and replaced at various times after induction as described in the text. Open boxes represent IDUA activity in extracts prepared from induced tissue after incubation in buffer. Shaded boxes represent the IDUA activity in the incubation buffer. Panel B: IDUA-9 plant tissue was induced and incubated without buffer for 34 hours after which an extract was prepared from the induced tissue. The IDUA activity of the extract is shown.

Figure 17B:
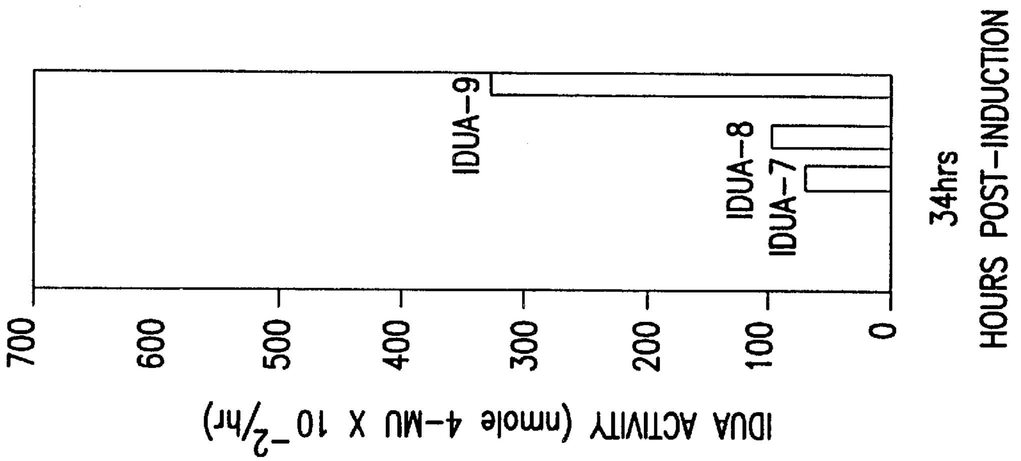
Figure 17A:
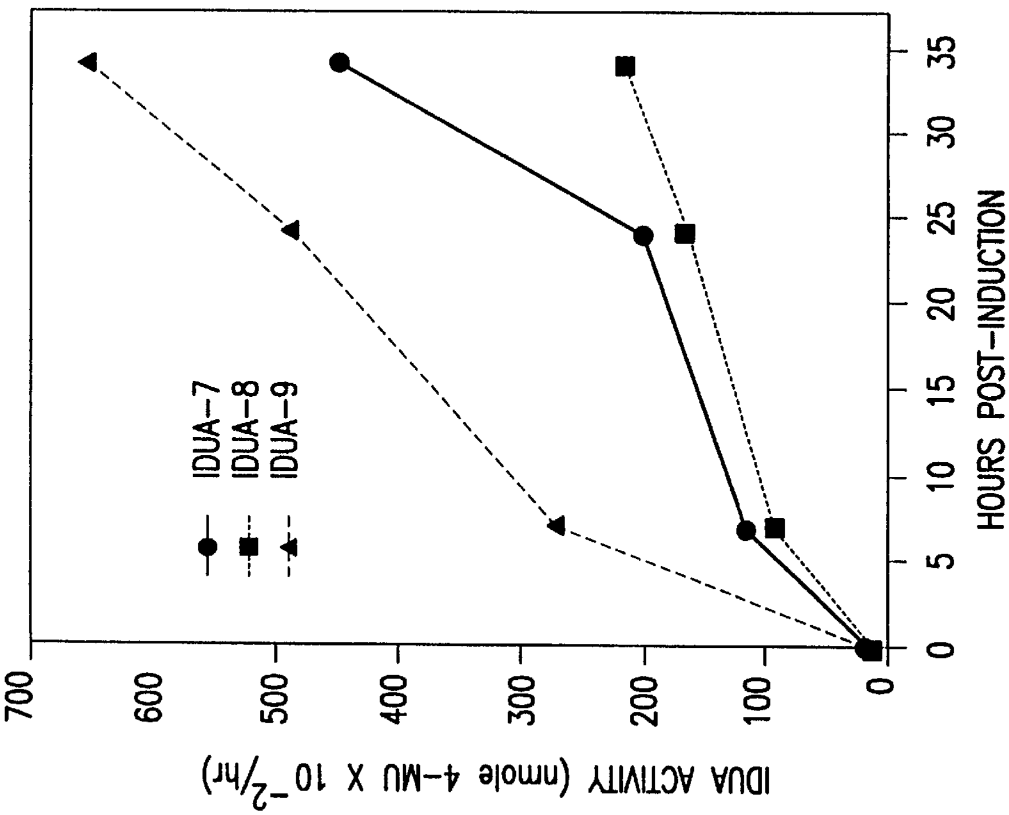

FIG. 17. Comparison of IDUA activity in transgenic tobacco plants IDUA-7, IDUA-8 and IDUA-9: Panel A: Plant tissue was induced and incubated in buffer, which was collected and replaced at various times after induction as described in the text. IDUA activity present in the incubation buffer collected at various times post-indlucton was plotted. Panel B: Plant tissue was induced and incubated without buffer absence of incubation buffer for 34 hours, after which extracts were prepared from the induced tissues. The IDUA activities of the extracts are shown.

Figure 18:
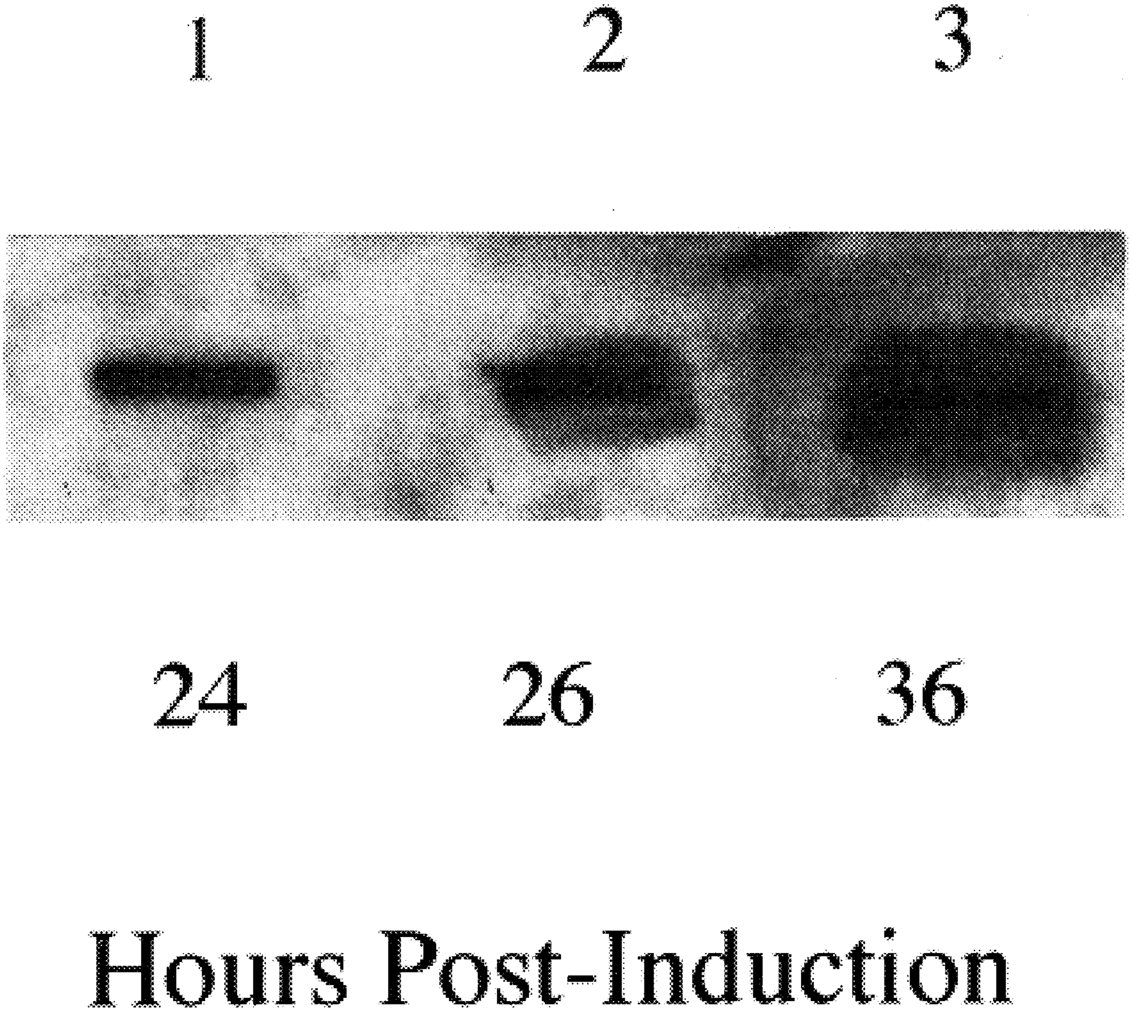

FIG. 18. Western slot blot analysis of secreted IDUA from transgenic plant IDUA-9 after three sequential addition and collection of incubation buffer; 24, 26 and 34 hrs post-MGA. The tissue (1.5 gm) was induced and incubated in a moist plastic bag for 24 hrs. Ten ml of incubation buffer was used to wash the tissue; this fraction is denoted as 24 hrs. Fresh buffer (10 ml) was added and incubated at room temperature for 2 hrs; this fraction was denoted as 26 hrs. Fresh buffer (10 ml) was added to the tissue and incubated for 8 hrs and this fraction was denoted as 34 hrs. Fifty μL of incubation buffer from each fraction was boiled and slotted onto OPTITRAN membrane and analyzed with anti-IDUA antibodies.

FIG. 19. The nucleotide sequence of the IDUA coding sequence (SEQ ID NO:8) used in the MeGA:IDUA and $35S^{ENH}$:IDUA expression construct.

FIG. 20. The deduced amino acid sequence (SEQ ID NO:9) of the IDUA coding sequence shown in FIG. 19.

Figure 21:
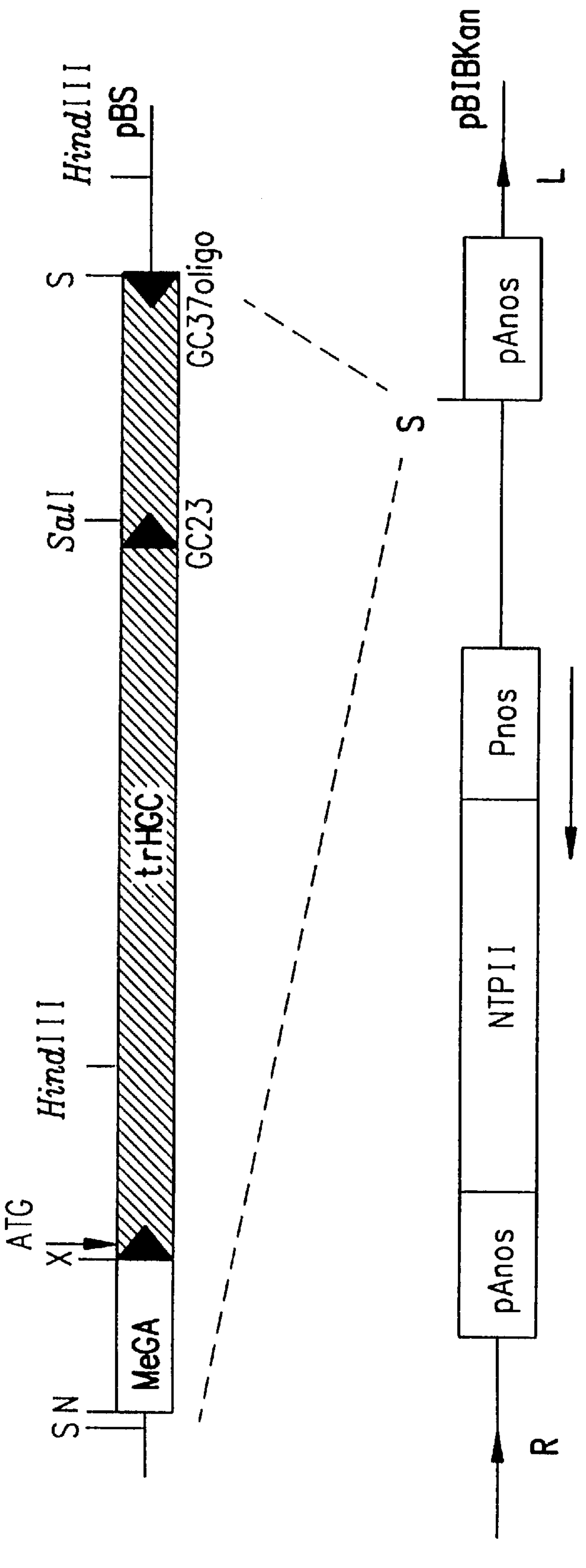

FIG. 21. hGC cDNA plant expression construct and transformation vector. The MeGA:hGC expression construct in a pBS intermediate plasmid is excised and inserted into the SstI site of the binary plant transformation vector pBIB-KAN to form transformation vector pCT50. The PCR-amplif.ication primers for reconstruction of the 3' end of the hGC coding region were: GC23, which has the sequence 5'GCCTATGCTGAGCACAAGTTACAG3' (SEQ ID NO:11); and GC37, whose complementary strand has the sequence 5'TTCCTTGAGCTCGTCACTGGCGACGCCA-CAGGTA3' (SEQ ID NO:12). The other abbreviations and notations shown are same as those described for FIG. 1.

5. DETAILED DESCRIPTION OF THE INVENTION

The present invention relates to the production of recombinant human or animal lysosomal enzymes in plants and in cultured plant cells and plant tissues, involving: (1) construction of recombinant expression constructs comprising lysosomal enzyme coding sequences and transformation vectors containing the expression constructs; (2) transforming or transfecting plant cells, plant tissues or plants with the transformation vectors; (3) expressing the lysosomal enzyme coding sequences in the plant cell, plant tissue or plant; and (4) detecting and purifying expression products having lysosomal enzyme activity.

The plant expression systems and the recombinant lysosomal enzymes produced therewith have a variety of uses, including but not limited to: (1) the production of enzymatically active enzymes for the treatment of lyisosomal storage diseases; (2) the production of antibodies against lysosomal enzymes, which antibodies would have medical diagnostic uses; (3) use in any commercial process that involves substrate hydrolysis; and (4) the production of modified proteins or peptide fragments to serve as precursors or substrates for further in vivo or in vitro processing to a specialized industrial form for research or therapeutic uses, such as to produce a therapeutic enzyme with increased efficacy or altered substrate specificity. These plant-expressed recombinant lysosomal protein products need not be enzymatically active or identical in structure to the corresponding native animal or human lysosomal enzymes or proteins in order to be useful for research or industrial applications.

The terms "lysosomal enzyme" and "lysosomal enzyme gene product," as used herein with respect to any such enzyme and product produced in a plant expression system, refer to a recombinant peptide expressed in a transgenic plant or plant cell from a nucleotide sequence encoding a human or animal lysosomal enzyme, a modified human or animal lysosomal enzyme, or a fragment, derivative or modification of such enzyme. Useful modified human or animal lysosomal enzymes include but are not limited to human or animal lysosomal enzymes having one or several naturally-occuring or artifically-introduced amino acid additions, deletions and/or substitutions.

The term "lysosomal enzyme coding sequence," as used herein, refers to a DNA or RNA sequence that encodes a protein or peptide, or a fragment, derivative or other modification thereof, which exhibits detectable enzymatic activity against a lysosomal enzyme substrate.

The term "enzymatically active" is used herein with respect to any recombinant lysosomal enzyme produced in a plant expression system to mean that the recombinant lysosomal enzyme is able to hydrolyze either the natural substrate, or an analogue or synthetic substrate thereof of the corresponding human or animal lysosomal enzyme, at detectable levels.

The term "enzymatically active" is also used herein with respect to recombinant hGC and modified hGC produced in a plant expression system to mean that such hGCs are able to hydrolyze the native hGC substrate, i.e., N-acyl-shingosyl-1-O-β-D-glucoside, of the hGC or that it can cleave the synthetic β-glucoside, 4-methyl-umbelliferyl-β-D-glucoside (4MuGlc), at detectable levels. Similarly, the term as applied to plant-produced IDUA and modified IDUA means that such IDUAs are able to hydrolyze the native IDUA substrate, i.e., dermatan sulfate or heparan sulfate, or is able to cleave the synthetic α-glucoside, 4-methylumbelliferyl-α-L-iduronide (4-MUI), at detectable levels.

The term "transformant" as used herein refers to a plant, plant cell or plant tissue to which a gene construct comprising a lysosomal enzyme coding sequence has been introduced by a method other than transfection with an engineered virus.

The term "transfectant" refers to a plant, plant cell or plant tissue that has been infected with an engineered virus and stably maintains said virus in the infected cell.

Once a plant transformant or transfectant is identified that expresses a recombinant lysosomal enzyme, one non-limiting embodiment of the invention involves the clonal expansion and use of that transformant or transfectant in the production and purification of enzymatically active recombinant lysosomal enzyme. In another non-limiting embodiment of the invention, each new generation of progeny plants may be newly screened for the presence of nucleotide sequence coding for a lysosomal enzyme, wherein such screening results in production by subsequent generations of plants of recoverable amounts of active recombinant lysosomal enzyme, and wherefrom the enzyme is then purified.

The invention is divided into the following sections solely for the purpose of description: (a) genes or coding sequences for lysosomal enzymes involved in lysosomal storage diseases; (b) construction of recombinant expression constructs for expressing lysosomal enzyme coding sequences in plant cell; (c) construction of plant transformation vectors comprising the expression constructs; (d) transformation/transfection of plants capable of translating and processing primary translation products in order to express an enzymatically active recombinant lysosomal enzyme; (e) identification and purification of the recombinant lysosomal enzyme so produced; (f) expansion of the number of transformed or transfected plants; and (g) methods of therapeutically using the recombinant lysosomal enzyme.

5.1. GENES OR CODING SEQUENCES FOR ENZYMES INVOLVED IN LYSOSOMAL STORAGE DISEASES

The recombinant lysosomal enzymes produced in accordance with this invention will have a variety of uses, probably the most significant being their use in enzyme replacement therapy for lysosomal storage diseases. These lysosomal enzymes include but are not limited to: α-N-acetylgalactosaminidase (Warner et al., Biochem. Biophys. Res. Commun., 1990, 173:13–19; acid lipase; aryl sulfatase A; aspartylglycosaminidase; ceramidase; α-L-fucosidase (de Wet et al., 1984, DNA 3:437–447), α-galactosidase, β-galactosidase, galactosylceramidase, glucocerebros:dase, α-glucosidase, β-glucuronidase, heparin N-sulfatase, β-hexosaminidase, iduronate sulfatase, α-L-iduronidase, α-mannosidase, β-mannosidase, sialidase, and sphingomyelinase. Of these enzymes, cDNAs have been cloned for α-N-acetylgalactosaminidase (Zhu & Goldstein, 1993, Gene 137:309–314); acid lipase (Amesis et al., 1994, Eur. J. Biochem 219:905–914); α-galactosidase (Eng & Desnick, 1994, Hum Mutat. 3:103–111); human glucocerebrosidase (hGC) (Sorge et al., 1985, supra); α-L-iduronidase (Scott et al., 1991, Proc. Natl. Acad. Sci. USA 88:9695–9699); iduronate sulfatase (Daniele et al., 1993, Genomics 16:755–757); α-mannosidase (Schatzle et al., 1992, J. Biol. Chem 267:4000–4007); and sialidase (Ferrari et al., 1994, Glycobiology 4:2047–2052).

The nucleic acid sequences encoding lysosomal enzymes which can be used in accordance with the invention include but are not limited to any nucleic acid sequence that encodes a lysosomal enzyme, modified lysosomal enzyme, or functional equivalent thereof, including but not limited to: (a) any nucleotide sequence that selectively hybridizes to the complement of a human or animal lysosomal enzyme coding sequence under stringent conditions, e.g., washing in 0.1×SSC/0.1% SDS at 68° C. (Ausubel et al., eds., 1989, *Current Protocols in Molecular Biology, Vol. I*, Greene Publishing Associates, Inc. and John Wiley & Sons, Inc., New York, at page 2.10.3), and encodes a product homologous to the human or animal lysosomal enzyme; and/or (b) any nucleotide sequence that hybridizes to the complement of the human or animal lysosomal enzyme coding sequence under less stringent conditions, such as moderately stringent conditions, e.g., washing in 0.2×SSC/0.1% SDS at 42° C. (Ausubel et al., 1989, supra), yet which still encoders a homologous gene product that is enzymatically active; and (c) any nucleotide coding sequence that otherwise encodes) a protein from any organism capable of hydrolyzing a human or animal lysosomal enzyme's native substrate or substrate analogue.

The invention also includes but is not limited to: (a) DNA vectors that contain any of the foregoing nucleotide coding sequences and/or their complements; (b) DNA expression and transformation vectors that contain expression constructs comprising any of the foregoing nucleotide coding sequences operatively associated with a regulatory element that directs expression of the coding sequences in plant cells or plants; and (c) genetically engineered plant cells or plants that contain any of the foregoing coding sequences, operatively associated with a regulatory element that directs the expression of the coding and/or antisense sequences in the plant cell. As used herein, the term "regulatory element" includes but is not limited to inducible and non-induacible promoters, enhancers, operators and other elements known to those skilled in the art that drive and/or regulate gene expression. The invention also includes fragments, derivatives or other modifications of the DNA sequences described herein.

5.2. TRANSFORMATION VECTORS TO DIRECT THE EXPRESSION OF LYSOSOMAL ENZYME CODING SEQUENCE

5.2.1. LYSOSOMAL ENZYME EXPRESSION CONSTRUCTS

In order to express a lysosomal enzyme in a plant expression system, the lysosomal enzyme coding sequence is inserted into an appropriate expression construct and the expression construct is incorporated into a transformation vector for transfer into cells of the plant. The expression construct is preferably constructed so that the lysosomal enzyme coding sequence is operatively associated with one or more regulatory elements, including, e.g., promoters and/or enhancers, necessary for transcription and translation of the lysosomal enzyme coding sequence. Methods to construct the expression constructs and transformation vectors include standard in vitro genetic recombination and manipulation. See, for example, the techniques described in Weissbach and Weissbach, 1988, *Methods For Plant Molecular Biology*, Academic Press, Chapters 26–28.

Regulatory elements that may be used in the expression constructs include promoters which may be either heterologous or homologous to the plant cell. The promoter may be a plant promoter or a non-plant promoter which is capable of driving high levels transcription of a linked sequence in plant cells and plants. Non-limiting examples of plant promoters that may be used effectively in practicing the invention include cauliflower mosaic virus (CaMV) 35S, rbcS, the promoter for the chlorophyll a/b binding protein, AdhI, NOS and HMG2, or modifications or derivatives thereof. The promoter may be either constitutive or inducible. For example, and not by way of limitation, an inducible promoter can be a promoter that promotes expression or increased expression of the lysosomal enzyme nucleotide sequence after mechanical gene activation (MGA) of the plant, plant tissue or plant cell. One non-limiting example of such an MGA-inducible plant promoter is MeGA (described infra).

The expression constructs can be additionally modified according to methods known to those skilled in the art to enhance or optimize heterologous gene expression in plants and plant cells. Such modifications include but are not limited to mutating DNA regulatory elements to increase promoter strength or to alter the lysosomal enzyme ccding sequence itself. Other modifications include deleting intron sequences or excess non-coding sequences from the 5' and/or 3' ends of the lysosomal enzyme coding sequence in order to minimize sequence- or distance-associated negative effects on expression of hGC, e.g., by minimizing or eliminating message destabilizing sequences.

The expression constructs may be further modifies according to methods known to those skilled in the art to add, remove, or otherwise modify peptide signal sequences to alter signal peptide cleavage or to increase or change the targeting of the expressed lysosomal enzyme through the plant endomembrane system. For example, but not by way of limitation, the expression construct can be specifically engineered to target the lysosomal enzyme for secretion, or vacuolar localization, or retention in the endoplasmic reticulum (ER).

In one embodiment, the expression construct can be engineered to incorporate a nucleotide sequence that encodes a signal targeting the lysosomal enzyme to the plant vacuole. For example, and not by way of limitation, the N-terminal 143 amino acid domain derived from the plant vacuolar protein, proaleurain (Holwerda et al., 1992, supra; Holwerda et al., 1990, supra), may be engineered into the expression construct to produce a signal peptide-lysosomal enzyme fusion product upon transcription and translation. The proaleurain signal peptide will direct the lysosomal enzyme to the plant cell vacuole, but is itself cleaved off during transit through the plant endomembrane system to generate the mature protein.

In another non-limiting embodiment, a signal peptide may be engineered into the expression construct to direct the lysosomal enzyme to be secreted from the plant cell. For example, and not by way of limitation, the signal peptide of tobacco PR-1, which is a secreted pathogenesis-related protein (Cornelissen et al., 1986, EMBO J. 5:37–40), can be engineered into the expression construct to direct the secretion of the lysosomal enzyme from the plant cell.

In an additional non-limiting embodiment, the signal peptide may be engineered into the expression construct to direct the lysosomal enzyme to be retained within the ER. Such ER-retained lysosomal enzymes may exhibit altered, and perhaps preferable, glycosylation patterns as a result of failure of the peptide to progress through the Golgi apparatus, thus resulting in a lack of subsequent glycosyl processing. For example, and not by way of limitation, a nucleotide sequence can be engineered into the expression construct to result in fusion of the amino acid sequence KDEL (SEQ ID NO:15), i.e., Lys-Asp-Glu-Leu, to the carboxyl-terminus of the lysosomal enzyme. The KDEL sequence results in retention of the lysosomal enzyme in the ER (Pfeffer and Rothman, 1987, Ann. Rev. Biochem. 56:829–852).

Expression construct may be further modified according to methods known to those skilled in the art to add coding sequences that facilitate purification of the lysosomal enzyme. In one non-limiting embodiment, a nucleotide sequence coding for the target epitope of a monoclonal antibody may be engineered into the expression construct in operative association with the regulatory elements and situated so that the expressed epitope is fused to the lysosomal enzyme. For example, and not by way of limitation, a nucleotide sequence coding for the FLAG™ epitope tag (International Biotechnologies, Inc., IBI), which is a hydrophilic marker peptide, can be inserted by standard techniques into the expression construct at a point corresponding to the carboxyl-terminus of the lysosomal enzyme. The expressed FLAG™ epitope-lysosomal enzyme fusion product may then be detected and affinity-purified using anti-FLAG™ antibodies.

In another non-limiting embodiment, a nucleotide sequence can be engineered into the expression construct to provide for a cleavable linker sequence between the lysosomal enzyme peptide sequence and any targeting signal, reporter peptide, selectable marker, or detectable marker, as described supra, that has not otherwise been cleaved from the lysosomal enzyme peptide sequence during peptide processing and trafficking through the plant endomembrane system. Such a linker sequence can be selected so that it can be cleaved either chemically or enzymatically during purification of the lysosomal enzyme (Light et al., 1980, Anal. Biochem. 106:199–206).

5.2.2. PLANT TRANSFORMATION VECTORS

The transformation vectors of the invention may be developed from any plant transformation vector known in the art include, but are not limited to, the well-known family of Ti plasmids from Agrobacterium and derivatives thereof, including both integrative and binary vectors, and including but not limited to pBIB-KAN, pGA471, pEND4K, pGV3850, and pMON505. Also included are DNA and RNA plant viruses, including but not limited to CaMV, geminiviruses, tobacco mosaic virus, and derivatives engineered therefrom, any of which can effectively serve as vectors to transfer a lysosomal enzyme coding sequence, or functional equivalent thereof, with associated regulatory elements, into plant cells and/or autonomously maintain the transferred sequence. In addition, transposable elements may be utilized in conjunction with any vector to transfer the coding sequence and regulatory sequence into a plant cell.

To aid in the selection of transformants and transfectants, the transformation vectors may preferably be modified to comprise a coding sequence for a reporter gene product or selectable marker. Such a coding sequence for a reporter or selectable marker should preferably be in operative association with the regulatory element coding sequence described supra.

Reporter genes which may be useful in the invention include but are not limited to the β-glucuronidase (GUS) gene (Jefferson et al., 1986, Proc. Natl. Acad. Sci. USA, 83:8447), and the luciferase gene (Ow et al., 1986, Science 234:856). Coding sequences that encode selectable markers which may be useful in the invention include but are not limited to those sequences that encode gene products conferring resistance to antibiotics, anti-metabolites or herbicides, including but not limited to kanamycin, hygromycin, streptomycin, phosphinothricin, gentamicin, methotrexate, glyphosate and sulfonylurea herbicides, and include but are not limited to coding sequences that encode enzymes such as neomycin phosphotransferase II (NPTII), chloramphenicol acetyltransferase (CAT), and hygromycin phosphotransferase I (HPT, HYG).

5.3. TRANSFORMATION/TRANSFECTION OF PLANTS

A variety of plant expression systems may be utilized to express the lysosomal enzyme coding sequence or its functional equivalent. Particular plant species may be selected from any dicotyledonous, monocotyledonous species, gymnospermous, lower vascular or non-vascular plant, including any cereal crop or other agriculturally important crop. Such plants include, but are not limited to, alfalfa, Arabidopsis, asparagus, barley, cabbage, carrot, celery, corn, cotton, cucumber, flax, lettuce, oil seed rape, pear, peas, petunia, poplar, potato, rice, soybean, sugar beet, sunflower, tobacco, tomato, wheat and white clover.

Methods by which plants may be transformed or transfected are well-known to those skilled in the art. See, for example, *Plant Biotechnology*, 1989, Kung & Arntzen, eds., Butterworth Publishers, ch. 1, 2. Examples of transformation methods which may be effectively used in the invention include but are not limited to Agrobacterium-mediated transformation of leaf discs or other plant tissues, microinjection of DNA directly into plant cells, electroporation of DNA into plant cell protoplasts, liposome or spheroplast fusion, microprojectile bombardment, and the transfection of plant cells or tissues with appropriately engineered plant viruses.

Plant tissue culture procedures necessary to practice the invention are well-known to those skilled in the art. See, for example, Dixon, 1985, *Plant Cell Culture: A Practical Approach*, IRL Press. Those tissue culture procedures that may be used effectively to practice the invention include the production and culture of plant protoplasts and cell suspensions, sterile culture propagation of leaf discs or other plant tissues on media containing engineered strains of transforming agents such as, for example, Agrobacterium or plant virus strains and the regeneration of whole transformed plants from protoplasts, cell suspensions and callus tissues.

The invention may be practiced by transforming or transfecting a plant or plant cell with a transformation vector containing an expression construct comprising a coding sequence for the lysosomal enzyme and selecting for transformants or transfectants that express the lysosomal enzyme. Transformed or transfected plant cells and tissues may be selected by techniques well-known to those of skill in the art, including but not limited to detecting repo-ter gene products or selecting based on the presence of one of the selectable markers described supra. The transformed or transfected plant cells or tissues are then grown and whole plants regenerated therefrom. Integration and maintenance of the lysosomal enzyme coding sequence in the plant genome can be confirmed by standard techniques, e.g., by Southern hybridization analysis, PCR analysis, including reverse transcriptase-PCR (RT-PCR), or immunological assays for the expected protein products. once such a plant transfcrmant or transfectant is identified, a non-limiting embodiment of the invention involves the clonal expansion and use of that transformant or transfectant in the production of lysosomal enzyme.

As one non-limiting example of a transformation procedure, Agrobacterium-mediated transformation of plant leaf disks can follow procedures that are well known to those skilled in the art. Briefly, leaf disks can be excised from axenically grown plant seedlings, incubated in a bacterial suspension, for example, $10^9$ cfu/ml, of *A. tumefaciens* containing an engineered plasmid comprising a selectable marker such as, for example, kanamycin resistance, and transferred to selective "shooting" medium containing, for example, kanamycin, that will block growth of bacteria and untransformed plant cells and induce shoot initiation and leaf formation from transformed cells. Shoots are regenerated and then transferred to selective media tc trigger root initiation. Stringent antibiotic selection at the rooting step is useful to permit only stably transformed shoots to generate roots. Small transgenic plantlets may then be transferred to sterile peat, vermiculite, or soil and gradually hardened off for growth in the greenhouse or in the field.

5.4. IDENTIFICATION AND PURIFICATION OF THE LYSOSOMAL ENZYME GENE PRODUCT

Transcription of the lysosomal enzyme coding sequence and production of the lysosomal enzyme in transformed or transfected plants, plant tissues, or plant cells can be confirmed and characterized by a variety of methods known to those of skill in the art. Transcription of the lysosomal enzyme coding sequence can be analyzed by standard techniques, including but not limited to detecting the presence of lysosomal enzyme messenger ribonucleic ac(id (mRNA) transcripts in transformed or transfected plants or plant cells using Northern hybridization analysis or RT-PCR amplification.

Detection of the lysosomal enzyme itself can be carried out using any of a variety of standard techniques, including, but not limited to, detecting lysosomal enzyme activity in plant extracts, e.g., by detecting hydrolysis either of the enzyme's natural substrate or a substrate analogue. Additionally, the lysosomal enzyme can be detected immunologically using monoclonal or polyclonal antibodies, or immuno-reactive fragments or derivatives thereof, raised against the enzyme, e.g., by Western blot analysis, and limited amino acid sequence determination of the protein.

Indirect identification of enzyme production in a plant can be performed using any detectable marker or reporter linked to the lysosomal enzyme. For example, but not by way of limitation, the FLAG™ epitope, which can be linked to the lysosomal enzyme, as described supra, is detectable in plant tissues and extracts using anti-FLAG M2 monoclonal antibodies (IBI) in conjunction with the Western Exposure™ chemi-luminescent detection system (Clontech).

Lysosomal enzyme production in a transformed or transfected plant can be confirmed and further characterized by histochemical localization, the methods of which are well-known to those skilled in the art.. See, for example, *Techniques in Immunocytochemistry, Vol I*, 1982, Bullock and Petrusz, eds., Academic Press, Inc. For example, but not by way of limitation, either fresh, frozen, or fixed and embedded tissue can be sectioned, and the sections probed with either polyclonal or monoclonal primary antibodies raised against the lysosomal enzyme or, for example, anti-FLAG™ monoclonal antibodies. The primary antibodies can then be detected by standard techniques, e.g., using the biotinylated protein A-alkaline phosphatase-conjugated streptavidin technique, or a secondary antibody bearing a detectable label that binds to the primary antibody.

The expression products can be further purified and characterized as described in the subsections below.

5.4.1. PRODUCTION AND PURIFICATION OF THE LYSOSOMAL ENZYME GENE PRODUCT

One non-limiting method to produce and purify the lysosomal enzyme is described here, wherein the lysosomal enzyme coding sequence is operably associated with an inducible promoter in the expression construct. Leaf or other tissue or cells from a transgenic plant or cell culture transformed or transfected with this expression construct can be processed to induce expression of the lysosomal enzyme coding sequence. This induction process may include inducing the activation of lysosomal genes by one or more methods, applied separately or in combination, including but not limited to physical wounding or other mechanical gene activation (MGA), and application of chemical or pathogenic elicitors or plant hormones. Lysosomal gene activation levels may also be enhanced in plant cells or tissues by factors such as the availability of nutrients, gases such as $O_2$ and $CO_2$, and light or heat. After induction of expression, the tissue can be stored, e.g., at −20° C. If the lysosomal protein is targeted for localization within the plant cell, the plant cell wall must be penetrated to extract the protein. Accordingly, the plant tissue can be ground to a fine powder, e.g., by using a tissue grinder and dry ice, or homogenized with a ground glass tissue homogenizer. To resuspend the lysosomal enzyme, plant membranes must be solubilized using an extraction buffer containing a detergent, e.g., a bile detergent such as 1% (w/v) sodium taurocholate, in a buffered solution, e.g., 25 mM sodium citrate, pH 7.0. The homogenate can then be clarified by, for example, centrifugation at 10,000×g for 30 min to produce a cell-free homogenate.

The lysosomal enzyme must be further purified ilf it is to be useful as a therapeutic or research reagent. The lysosomal enzyme can be purified from plant extracts according to methods well-known to those of skill in the art (Furbish et al., 1977, Proc. Natl. Acad. Sci. USA 74:3560–3563). Once the presence of the enzyme is confirmed it can be isolated from plant extracts by standard biochemical techniques including, but not limited to, differential ammonium sulfate (AS) precipitation, gel filtration chromatography or affinity chromatography, e.g., utilizing hydrophobic, immunological or lectin binding. At each step of the purification process the yield, purity and activity of the enzyme can be determined by one or more biochemical assays, including but not limited to: (1) detecting hydrolysis of the enzyme's substrate or a substrate analogue; (2) immunological analysis by use of an enzyme-linked immunosorbent assay (ELISA); (3) sodium dodecyl sulfate-polyacrylamide gel electrophoresis (SDS-PAGE) analysis; and (4) Western analysis. The enzyme may be alternatively or additionally purified by affinity chromatography wherein the enzyme binds to its inhibitor which is linked, for example, to an inert substrate.

Once solubilized, all enzyme-containing fractions can be maintained, for example, by storage at 4° C., and stabilized if necessary, e.g., with 4 mM β-mercaptoethanol, 5 mM EDTIA, and/or possibly with high levels of glycerol or ethylene glycol.

5.4.2. PROTEOLYTIC PROCESSING OF THE SIGNAL PEPTIDE

In order to address whether the plant expression system efficiently recognizes and correctly cleaves the human signal peptide from the lysosomal enzyme, the plant-produced enzyme can be purified and analyzed by N-terminal sequencing. Accordingly, the enzyme can, for example, be treated with Endo-F/N-glucanase (Boehringer Mannheim) to remove N-linked glycans, and the resulting peptide can be repurified by methods described supra. The purity of the enzyme can be determined based, for example, on silver-stained SDS-PAGE. The band containing the enzyme can be excised from the gel, the peptide eluted therefrom, and then analyzed by commercial N-terminal amino acid sequencing to determine whether the correct cleavage of the signal peptide has occurred. Incomplete cleavage can be detected, for example, as a double band on SDS-PAGE, or as mixed N-terminal sequences.

5.4.3. N-LINKED GLYCOSYLATION IN PLANTS VERSUS ANIMALS

The oligosaccharides of native human and animal lysosomal enzymes are typical antennary structures containing N-acetylglucosamine, mannose, and sialic acid. The glycoconjugate associated with the lysosomal enzyme of the invention may be determined, for example, by lectin binding studies (Reddy et al., 1985, Biochem. Med. 33:200–210, Cummings, 1994, Meth. Enzymol. 230:66–86).

Plant glycans do not contain sialic acid, which is a prevalent terminal sugar in mammalian glycans. In addition, the complex glycans of plants are generally smaller and contain a β1-2 xylose residue attached to the β-linked mannose residues of the core (Gomez and Chrispeels, 1994, Proc. Natl. Acad. Sci. USA 91:1829–1833).

Determination of the glycan composition and structure of the lysosomal enzyme of the invention is of particular interest because: (a) the glycan composition will indicate the status of the protein's movement through the Golgi; and (b) the presence of a complex glycan may indicate whether an antigenic response will be triggered in humans.

Several molecular, genetic and chemical approaches can be used to raise the proportion of the high-mannose form of glycans on lysosomal enzymes, making them more similar in structure to the native human protein (Grabowski et al., 1995, Ann. Int. Med. 122:33–39; Berg-Fussman et al., 1993, J. Biol. Chem. 268:14861–14866). For example, but not by way of limitation, the mannose analog, 1-deoxymannojirimycin (dMM), inhibits mannosidase I, the first Golgi-specific enzyme involved in glycan processing. Plant tissues treated with dMM produce glycoproteins which lack fucose and xylose and maintain a glycan profile consistent with inhibition at the mannosidase I step (Vitale et al., 1989, Pl. Phys. 89:1079–1084). Treatment of lysosomal enzyme-expressing plant tissues with dMM may be useful to produce lysosomal enzymes with a relatively homogeneous high-mannose glycan profile. Such lysosomal enzymes should be highly effective for use in treatment of lysosomal storage diseases in human and animals.

5.5. CLONAL PROPAGATION AND BREEDING OF TRANSGENIC PLANTS

Once a transformed or transfected plant is selected that produces a useful amount of the recombinant lysosomal enzyme of the invention, one embodiment of the invention contemplates the production of clones of this plant either by well-known asexual reproductive methods or by standard plant tissue culture methods. For example, tissues from a plant of interest can be induced to form genetically identical plants from asexual cuttings. Alternatively, callus tissue and/or cell suspensions can be produced from such a plant and subcultured. An increased number of plants can subsequently be regenerated therefrom by transfer to the appropriate regenerative culture medium.

Alternatively, the recombinant lysosomal enzyme-producing plant may be crossed as a parental line, either male or female, with another plant of the same species or variety, which other plant may or may not also be transgenic for the lysosomal coding sequence, to produce an F1 generation. Members of the F1 and subsequent generations can be tested, as described supra, for the stable inheritance and maintenance of the lysosomal enzyme coding sequence, as well as for lysosomal enzyme production. A breeding program is thus contemplated whereby the lysosomal enzyme coding sequence may be transferred into other plant strains or varieties having advantageous agronomic characteristics, for example, by a program of controlled backcrossing. The invention thus encompasses parental lines comprising the lysosomal enzyme coding sequence, as well as all plants in subsequent generations descending from a cross in which at least one of the parents comprised the lysosomal enzyme coding sequence. The invention further encompasses all seeds comprising the lysosomal enzyme coding sequence and from which such plants can be grown, and tissue cultures, including callus tissues, cell suspensions and protoplasts, comprising the lysosomal enzyme coding sequence, whether or not they can be regenerated back to plants.

5.6. METHODS FOR THERAPEUTIC USE OF LYSOSOMAL ENZYMES

The recombinant lysosomal enzymes of the invention are useful for therapeutic treatment of lysosomal storage diseases by providing a therapeutic amount of a particular lysosomal enzyme, or a derivative or modification thereof, to a patient suffering from a lysosomal storage disease or condition resulting from a deficiency of the corresponding human or animal active form of that enzyme.

By "therapeutic amount" is meant an amount of enzymatically active lysosomal enzyme which will cause significant alleviation of clinical symptoms of a particular lysosomal storage disease.

A therapeutic amount causes "significant alleviation of clinical symptoms" of the particular lysosomal storage disease if it serves to reduce one or more of the pathological effects or symptoms of the disease or to reduce the rate of progression of one or more of such pathological effects or symptoms.

An effective dosage and treatment protocol may be determined by conventional means, starting with a low dose in laboratory animals and then increasing the dosage while monitoring the effects, and systematically varying the dosage regimen as well. The amount of recombinant lysosomal enzyme to be administered to a patient suffering from a lysoe;omal disease or condition will vary. Numerous factors may be taken into consideration by a clinician when determining an optimal dose for a given subject. These factors include the size of the patient, the age of the patient, the general condition of the patient, the particular disease being treated, the severity of the disease, the presence of other drugs in the patient, and the like. Trial dosages would be chosen after consideration of the results of animal studies, and any available clinical literature with respect to past results of replacement therapy for the particular lysosomal storage disease.

For example, therapeutic amounts of recombinant hGC and IDUA and modified hGC and IDUA produced according to the invention may in each instance encompass dosages of between about 10 and about 500 mg per 70 kg patient per month, depending upon the severity of the patient's symptoms of the Gaucher's or Hurler's disease.

The amount of recombinant lysosomal enzyme of the invention administered to the patient may be decreased or increased according to the enzymatic activity of the particular lysosomal enzyme. For example, administration of a recombinant lysosomal enzyme of the invention which has been modified to have increased enzymatic activity relative to the native human or animal enzyme will require administration of a lesser amount to the patient than a native human or animal lysosomal enzyme having lower enzymatic activity.

In addition, the amount of recombinant lysosomal enzyme administered to the patient may be modified over time depending on a change in the condition of the patient as treatment progresses, the determination of which is within the skill of the attending clinician.

The invention also provides pharmaceutical formulations for use of the recombinant lysosomal enzyme in treating lysosomal storage diseases. The formulations comprise a recombinant lysosomal enzyme of the invention and a pharmaceutically acceptable carrier. A variety of aqueous carriers may be used, e.g., water, buffered water, 0.4% saline, 0.3% glycine, and the like. The pharmaceutical formulations may also comprise additional components that serve to extend the shelf-life of pharmaceutical formulations, including preservatives, protein stabilizers, and the like. The formulations are preferably sterile and free of particulate matter (for injectable forms). These compositions may be sterilized by conventional, well-known sterilization techniques.

The compositions may contain pharmaceutically acceptable auxiliary substances as required to approximate physiological conditions, such as pH adjusting and buffering agents, toxicity adjusting agents and the like, e.g., sodium acetate, sodium chloride, potassium chloride, calcium chloride, sodium lactate, etc.

The formulations may be adapted for various forms of administration, including intramuscularly, subcutaneously, intravenously and the like. The subject formulations may also be formulated so as to provide for the sustained release of a lysosomal enzyme. Actual methods for preparing parenterally administrable compositions and adjustments necessary for administration to subjects will be known or apparent to those skilled in the art and are described in more detail in , for example, Remington's *Pharmaceutical Science*, 17*th Ed*., Mack Publishing Company, Easton, Pa. (1985), which is incorporated herein by reference.

The invention is illustrated in the working examples described infra, for the expression of hGC in tobacco.

6. EXAMPLE 1

PRODUCTION AND ISOLATION OF RECOMBINANT MODIFIED hGC FROM TRANSGENIC TOBACCO PLANTS

The subsections below describe the production of an enzymatically active modified human glucocerebrosidase (hGC) in tobacco.

6.1. CONSTRUCTION OF A MODIFIED hGC EXPRESSION CONSTRUCT AND INSERTION INTO A PLANT TRANSFORMATION VECTOR

6.1.1. PROMOTER:hGC EXPRESSION CONSTRUCT

*E. coli* containing the hGc cDNA sequence cloned from fibroblast cells, as described (Sorge et al., 1985, supra), was obtained from the ATCC (Accession No. 65696). Oligonucleotide primers GC1 (corresponding to the amino terminus of the hGC coding region as shown in FIG. 1), and GC4 (corresponding to the carboxy terminus of the hGC coding region), were used to amplify the hGC cDNA sequence using the polymerase chain reaction (PCR). Primer GC1 was designed to include the hGC ATG initiation codon and to generate a 5' XbaI site. Primer GC4, complementary to hGC mRNA, does not include the stop codon for the gene and was designed to generate an EcoRI restriction site. The design of oligonucleotide GC4 also corrected an altered base in the ATCC sequence (GenBank/EMBL #M11080), thus producing an Arg-Arg-Gln sequence upstream to the site where a FLAG™ epitope will be inserted.

The 1.9 kb fragment generated by PCR was purified by agarose gel elution, digested with XbaI and EcoRI, and ligated into the similarly digested plasmid, Bluescript $SK^-$ (Stratagene). This cloning vector was chosen because of its small size (2.9 kb) and its extensive multiple cloning region.

The MeGA promoter, comprising a 456 bp fragment (FIG. 11) (SEQ ID NO:5) as modified from the tomato HMG2 promoter (Weissenborn et al., 1995, Phys. Plantarum 93:393–400), was used to drive the expression of the hGC gene. The MeGA promoter is inducible and has a low basal expression in unstressed plant tissues, but is highly induced in both immature and mature tissues by the process of mechanical gene activation (MGA), or by a variety of chemicals that induce plant defense responses. MGA includes but is not limited to the mechanical shredding of leaf tissue, for example, into 2 mm strips, followed by storage at room temperature on Whatman 3 MM chromatography paper moistened with sterile water in a sealed plastic bag. The expression of a MeGA:GUS construct has been monitored in transgenic tobacco plants from seedling stage to flowering and it showed no loss of inducible activity as plants reached maturity.

The 456 bp MeGA promoter was PCR-amplified using primers which incorporated a NotI restriction site at the 5' end of the fragment and a XbaI site at the 3' end of the promoter. This fragment also contained the 5'-untranslated leader of its native tomato sequence and thus provided all necessary 5' elements for expression of the fused hGC sequences. Following amplification, the fragment was PAGE-purified, digested with NotI and XbaI, and ligated into the plasmid containing the hGC coding region, which had also been NotI/XbaI digested, to produce a MeGA:hGC fusion.

6.1.2. GENERATION OF A MeGA:hGC:FLAG™ CONSTRUCT

In order to facilitate detection and purification of the hGC gene product, a FLAG™ epitope coding sequence was fused in frame to the C-terminus of the hGC coding sequence. The FLAG™ epitope (IBI) is the octapeptide Asp-Tyr-Lys-Asp-Asp-Asp-Asp-Lys (or DYKDDDDK) (SEQ ID NO:10) designed to be a hydrophilic marker peptide situated on a protein surface to facilitate antibody interactions (Shelness, 1992, Epitope 1:11–17; Hopp et al., 1988, Bio/Tech. 6:1204–1210).

A double-stranded oligonucleotide (FIG. 1) was synthesized which incorporated: (a) a 5' EcoRI restriction site which creates an in-frame fusion with the engineered hGC C-terminus EcoRI site; (b) the FLAG™ octapeptide coding region; (c) a stop codon following the epitope; and (d) a 3' SstI/EcoRI site. The DNA encoding FLAG™ was PAGE-purified, digested with EcoRI, and the fragment encoding FLAG™ inserted into the EcoRI site of the MeGA:hGC plasmid, and tested for insert orientation.

The translational fusion was tested by in vitro transcription using T3 RNA polymerase driven by the T3 promoter in the pBluescript SK- vector following excision of the MeGA promoter, and in vitro translation in the presence of $^{35}S$-methionine using rabbit reticulocyte lysates (BRL). The major translation product was about 56–59 kDa, consistent with the expected size of the hGC:FLAG™ fusion product (59 kDa). In addition, the hGC:FLAG™ fusion construct was completely sequenced using the dideoxy-sequenase system (USB). The nucleotide sequence of the hGC:FLAG™ fusion (SEQ ID NO:3) is shown in FIG. 9; the deduced amino acid sequence (SEQ ID NO:4) is shown in FIG. 10. The construction altered amino acid residue 545 to an arginine (R) and added ten amino acid residues, including the FLAG™ octapeptide, to the carboxyterminal of hGC. See FIG. 10.

6.1.3. INSERTION OF THE MeGA:hGC:FLAG™ CONSTRUCT INTO A PLANT TRANSFORMATION VECTOR

The MeGA:hGC:FLAG™ expression construct was excised from the pBluescript vector by digestion with SstI and ligated into the corresponding restriction site in the multiple cloning region of the plant binary vector pBIB-KAN (Becker, 1990, Nucl. Acids Res. 18:203) to form plasmid CTPro1:hGC:FLAG™. As shown in FIG. 1, insertion of the MeGA:hGC:FLAG™ expression construct correctly positioned a plant transcriptional terminator for the construct. In addition, the binary vector carries an NPTII gene within the transfer DNA (T-DNA) which allows for selection of transformed plant cells based on kanamycin resistance. The engineered plasmid was transformed into *E. coli* strain DH5α and tested for correct insertion prior to mobilization into *Agrobacterium tumefaciens* strain LBA4404 (Hoekma et al., 1983, Nature 303:179–180).

6.2. INTRODUCTION OF THE MeGA:hGC:FLAG™ EXPRESSION CONSTRUCT INTO TOBACCO AND ASSESSMENT OF hGC:FLAG™ EXPRESSION 6.2.1. GENERATION OF TRANSGENIC TOBACCO PLANTS CONTAINING THE MeGA:hGC:FLAG™ CONSTRUCT

Agrobacterium-mediated transformation (Horsch et al., 1984, Science 223:496–498) was used to stably integrate the modified T-DNA sequence containing the MeGA:hGC:FLAG™ construct into the genome of tobacco. Leaf discs excised from aseptically grown seedlings of tobacco (*Nicotiana tabacum*) cvs. Xanthi (a non-commercial variety) and VA116 (a commercial, flue-cured variety) were briefly incubated in a bacterial suspension ($10^9$ cfu/ml) of *A. tumefaciens* containing the engineered plasmid (FIG. 2A), and co-cultivated on plates containing a nurse-culture of cultured tobacco cells for 48 hr. The leaf discs were then transferred to MS media (Murashige & Skoog, 1962, Physiol. Plant. 15:473–497) containing 100 mg/L kanamycin and 9.12 $\mu$M zeatin, which is a selective "shooting" medium that blocks the growth of bacteria and untransformed plant cells, and encourages shoot formation (Horsch et al., supra).

Shoots were observed three weeks post-inoculation (FIG. 2B) and were excised and placed on selective rooting media (100 mg/L kanamycin, 10 $\mu$M indole-3-acetic acid in MS media). After 1 week, the rooted plantlets (FIG. 2C) were transferred to sterile potting soil and placed in the greenhouse (FIG. 2D). Additional shoots were excised and rooted over the next 4 weeks with a total of 45 individual transformants being brought to soil (FIG. 2E). The presence of the gene construct did not appear to have any effect on the growth or development of these transformants.

6.2.2. SOUTHERN ANALYSIS OF MeGA:hGC:FLAG™ INSERTIONS IN TRANSGENIC PLANTS

The stable insertion of the MeGA:hGC:FLAG™ construct was confirmed by genomic Southern hybridization analysis. Total DNA was isolated from leaf tissue of eight young regenerants and digested with HindIII, which cuts only once within the introduced DNA (see FIG. 1). The second HindIII site flanks the introduced DNA and is located within the plant's genomic DNA. Thus, when probed with hGC cDNA sequences (1.7 kb HindIII fragment from pBluescript intermediate vector) 3' of the HindIII site, each fragment should be a distinctive size and represent an independent insertional event within the plant genome.

Five of the eight putative transformants tested showed multiple hGC inserts (FIG. 3). Four of these plants (X-1, X-8, X-9 and X-11) were derived from the Xanthi cultivar. One plant (V-1) was derived from cultivar VA116. Transformant X-8 had less DNA loaded and showed two bands upon longer autoradiographic exposure. In addition, high levels of hGC were detected in other transformants for which Southern hybridizations were not carried out, including a plant designated X-27.

6.2.3. NORTHERN ANALYSIS OF TRANSCRIPTIONAL ACTIVATION OF THE MeGA:hGC:FLAG™ TRANSGENE

As described supra, the MeGA promoter is essentially inactive in unstressed leaves, but is activated by MGA (see FIG. 4) or by treatment with chemicals that induce plant defense responses. In order to demonstrate that transgenic plants express hGC:FLAG™ mRNA in the expected inducible expression pattern, transformed plant tissue was induced by MGA, i.e., by shredding the leaf tissue into 2 mm strips, followed by incubation of Whatman #1 paper moistened with sterile water within a ZipLoc™ plastic bag and incubated at room temperature for 24 hrs. Total RNA was isolated by standard guanidino-thiocyanate methods from leaf tissue of untransformed and transformed plants immediately upon excision (time 0), or at 24 hr after MGA.

As shown in FIG. 4, hGC:FLAG™ mRNA levels were undetectable in leaves of X-11 at the time 0, but showed a marked increase in hGC transcript levels 24 hr after MGA. A more detailed time course of a second plant, V-1, showed detectable mRNA by 4 hr, maximal RNA levels at 24 hr, and mRNA levels declining at 48 hr. In addition, transcript levels increased in response to chemical defense elicitors compared to MGA. This pattern of expression is exactly that expected of a transgene construct linked to the MeGA promoter (Park et al., 1992, Pl. Mol. Biol. 20:327–331; Yang et al., 1991, Pl. Cell 3:397–405).

6.2.4. IMMUNODETECTION OF THE hGC:FLAG™ PROTEIN IN TRANSGENIC PLANT EXTRACTS

As described supra, the hGC:FLAG™ fusion construct was designed to utilize the FLAG™ epitope to facilitate detection and purification of the hGC:FLAG™ fusion protein. Seven weeks after plants were potted in soil, leaf discs from 35 plants of the 45 transformants described above were harvested (and thereby wounded) to induce transgene expression.

Extracts from the leaf discs of control plants and transgenic plants were spotted on nitrocellulose membranes for immuno-dot blot analysis. Monoclonal antibodies (anti-FLAG M2, IBI) against the FLAG™ epitope, in conjunction with the Western Exposure™ chemiluminescent detection system (Clontech, Inc.), were used to test for immuno-reactive material. Of the 35 plants tested, 25 showed significant transgene expression.

Western analysis of extracts from wounded leaves of untransformed plants and transformed plants were tested for immuno-reactivity to polyclonal antibodies raised against hGC (FIG. 5B). These antibodies have not shown binding to any mammalian proteins other than the acid β-glucosidase, i.e., glucocerebrosidase of chimpanzees. Extracts from transgenic plants showed strong immuno-reactivity by a single protein band with an apparent molecular weight of about 66–69 kDa (FIG. 5B). The size of the immuno-reactive protein wias reduced to about 58 kDa after N-glucanase treatment, indicating that the enzyme was glycosylated. Analogous Western immunoblots probed with anti-FLAG™ antibodies showed additional similar molecular weight bands (FIG. 5A), suggesting that both the polyclonal antibody to hGC and the anti-FLAG™ antibody recognize the same fusion protein product.

6.2.5. ENZYMATIC ACTIVITY IN TOBACCO EXTRACTS

Plant tissues were tested for hGC activity using a sensitive and convenient assay that is widely utilized in Gaucher disease research (Grabowski et al., 1990, in: *Critical Reviews in Biochemistry and Molecular Biology*, 25:385–414, CRC Press, Inc.). This assay uses the fluorometric substrate, 4-methylumbelliferyl-β-D-glucopyranoside (4MuGlc) (the "4MuGlc assay"). An increase in absorbance at 460 nm results from cleavage of 4MuGlc, and indicates the presence of enzymatic activity. 4MuGlc also serves as a substrate for endogenous plant β-glucosidases which have been detected in leaves of both control and transgenic plants. However, several distinctive properties of hGC were used to distinguish between endogenous glucosidase activity and hGC activity (TABLE 1). The differences in solubility together with the use of anti-FLAG™ affinity system for purification of the hGC-:FLAG™ were employed to solve the problem of separating hGC:FLAG™ from the endogenous plant β-glucosidases (Table 2, FIG. 8).

TABLE 1

Comparisons of endogenous tobacco β-glucosidase and hGC:FLAG ™

| CHARACTERISTICS | ENDOGENOUS | hGC:FLAG ™ |
|---|---|---|
| Solubility | Present in soluble extract in 0.1% Triton X-100 buffer | Membrane-associated, requiring high Triton concentration, sonication, or freeze/thaw to solubilize |
| Response to MGA | High levels in unstressed leaves, declines approx. 80% post-MGA | Absent in unstressed leaves, induced 24–48 hrs post-MGA |
| Inhibition | Weakly inhibited by conduritol B epoxide (CBE) (Sigma) | Strongly inhibited by CBE |
| Substrate | Active with MuGlc | Active with MuGlc |
| Antibody response | No immuno-reactivity to anti-FLAG ™ or anti-hGCase antibodies | Immuno-reactive to both anti-FLAG ™ and anti-hGCase antibodies |

6.2.6. ACCUMULATION OF hGC:FLAG™ PROTEIN IN TOBACCO TISSUES

In order to determine the best length of incubation time post-MGA for optimum yield of hGC:FLAG™ protein and hGC enzyme activity, extracts were analyzed from transgenic leaves at 0, 2, 4, 8, 16, and 24 hrs post-MGA. Plant tissue (0.5 gm) was ground using dry ice and a coffee bean grinder. To solubilize hGC:FLAG™, the ground tissue was resuspended in 1.0 ml of extraction buffer containing 25 mM sodium citrate pH 7.0, 1% (w/v) sodium taurocholate, 4 mM β-mercaptoethanol, and 5 mM EDTA. The homogenate was frozen in a dry ice/ethanol bath for 30 min and thawed at 4° C. for 2 hrs. This freeze-thaw procedure was repeated. Cell debris was pelleted at 14,000×g for 15 min. at 4° C. The cell free supernatant was collected and brought up to 40% (v/v) glycerol in order inhibit the denaturation of hGC:FLAG™ protein.

Western analysis was carried out on 10 μg of soluble protein from leaf extracts to test for immuno-reactivelty to polyclonal antibodies raised against hGC (FIG. 5B) and monoclonal antibodies against the FLAG™ epitope (FIG. 5A). The highest level of induction of hGC:FLAG™ protein occurred between 8 and 12 hrs post-MGA.

To determine the optimum time post-MGA for obtaining the highest level of hGc enzymatic activity, 0.1 μg of leaf extracts were assayed using the 4MuGlc assay. The highest hGC activity was found in extracts from 12 hrs post-wounded tissue (FIG. 6).

6.3. PURIFICATION OF hGC:FLAG™ FROM TOBACCO EXTRACTS

Forty gms of post-wounded (12 hrs) tissue was ground to a fine powder using dry ice and a coffee bean grinder. One hundred mls of extract buffer were added and the sample was made into a slurry using a polytron (Brinkman Scientific). The extract was frozen in a dry ice/ethanol bath for 1 hr and thawed for 16 hrs at 4° C. Cell debris was pelleted at 14,000×g for 30 min. The supernatant was filtered through it layers of cheese cloth and the filtrate was saved. An 1 ml aliquot was stored in 40% (v/v) glycerol for later protein and hGC enzymatic activity determination, while ammonium sulfate (AS) was gradually added with stirring to the remaining filtrate to 33% (w/v) final concentration and incubated at 4° C. for 1 hr. The homogenate was cleared by centrifugation at 14,000×g for 30 min. The supernatant was dialyzed overnight at 4° C. against the following buffer: 0.1M sodium citrate, pH 6.0, 4 mM β-mercaptoethanol and 5 mM EDTA. The supernatant was clarified by centrifugation at 14,000×g for 30 min. The cleared supernatant was concentrated (Amicon, YM30 filters) to a final volume of 5 mls, and 0.5 ml of the concentrated AS supernatant was saved for protein and hGC enzyme activity analysis. The hGC:FLAG™ in 1 ml of concentrated supernatant was purified by affinity chromatography using an anti-FLAG™ affinity column.

To utilize the FLAG™ epitope for purification of the hGC:FLAG™ protein, 1 ml of leaf extract prepared as above was applied to a 1 ml anti-FLAG™ M2 affinity column. The column was previously equilibrated with phosphate-buffered saline (PBS; 50 mM, pH 6.4) containing 10% glycerol and 4 mM β-mercapto-ethanol at 4° C. After several washes with PBS, the bound hGC:FLAG™ protein was eluted with three 1 ml aliquots of purified FLAG™ peptide (IBI), i.e., 1 ml at 500 μg/ml, followed by 2×1 ml at 250 μg/ml. Eluted material was slot-blotted onto a nitrocellulose membrane and tested for immuno-reactivity to the anti-FLAG™ M2 antibody, and analyzed by SDS-PAGE, and stained with Commassie blue to determine relative purity (FIG. 7A). No immuno-reactive material was eluted in the first fraction since release of the bound hGC:FLAG™ protein requires equilibration with the peptide. As a consequence, the second and third eluted fractions contained the majority of immuno-reactive material. SDS-PAGE analysis of anti-FLAG™-purified hGC:FLAG™ protein showed a single band co-migrating with the anti-FLAG™ immuno-reactive protein (FIG. 7A).

In order to utilize the properties of the glycans present on the hGC:FLAG™ protein for purification purposes, hGC:FLAG™ protein was also isolated using a concanavalin-A (ConA) affinity column (Sigma). Concentrated tissue extract (1.5 ml) was loaded onto a 1.5 ml bed volume of ConA in column buffer (0.1M sodium citrate pH 6.5, 0.15M sodium chloride). An equal volume of column buffer was added to the concentrated extract and passed through the column twice at 4° C. The ConA column was washed three times with column buffer using three times the bed volume of buffer. The bound hGC:FLAG™ was eluted with 5 mls of 0.1M methyl α-D-mannopyranoside (Sigma) followed by 5 mls of 1M methyl α-D-mannopyranoside. Fractions were collected and assayed for protein content and hGC enzymatic activity. All fractions containing hGC enzyme activity were concentrated (Amicon, YM30 filters) to a final volume of 0.5 ml. To stabilize the hGC enzymatic activty of the hGC:FLAG™ protein, the concentrated extract was made 40% (v/v) in glycerol and stored at 4° C. SDS-PAGE analysis of the ConA purified hGC:FLAG™ protein (FIG. 7B) showed a band migrating at 66–69 kd and three lower molecular weight bands that stained equally with Commassie blue.

Enzyme activity and protein determination of fractions from each step in the purification indicate that the most effective method to purify hGC:FLAGm was to employ anti-FLAG™ affinity chromatography followed by the ConA affinity chromatography (see Table 2 and FIGS. 7A–B).

TABLE 2

PURIFICATION OF hGC:FLAG ™ FROM TOBACCO EXTRACTS

| Fraction | Protein Conc. | Specific activity (nmole 4 MU/min/μg/ml) | % Activity Recovered | Fold Purification |
|---|---|---|---|---|
| 40 gms FW | 2 mg/ml | *0.027 | 100 | 1 |
| 33% AS-sup | 2.5 mg/ml | *0.625 | 180 | 13 |
| ConA | 0.1 mg/ml | +0.81 | 12.5 | 240 |
| FLAG | 7.2 μg/ml | +0.84 | N.D. | N.D. |

*Since 4 MUGlc is not a specific substrate, this specific activity represents both plant glucosidase and hGC activity.
+ Plant glucosidase does not bind to ConA or anti-FLAG ™ affinity columns (data not shown), therefore, this enzymatic activity is from hGC:FLAG ™ alone.

6.4. PRODUCTION OF hGC:FLAG™ PROTEIN FROM TOBACCO PLANTS

An estimation can be made on the amount of hGC: FLAG™ extracted per gm fresh weight of tobacco plant tissue or per mg soluble protein from slot blot western analysis of initial crude extracts using anti-FLAG™. Approximately 2 mg/ml of soluble protein were extracted per 0.5 gm of fresh weight plant tissue. Western slot blot analysis of 1 μl of crude extract indicates the presence of approximately 0.5 to 0.6 μg of hGC:FLAG™ (FIG. 8). Based on these results, a single mature tobacco plant comprising about 1.6 kg of fresh weight of tissue will contain about 2.5 gm of hGC:FLAG™ per plant. Accordingly, a standard acre of tobacco planted to 6,000 plants could potentially produce 15 kg of hGC:FLAG™ (Table 3).

TABLE 3

EXTRACTABLE hGC:FLAG ™ PER ACRE OF TOBACCO

| Tissue | Soluble Protein Total | Extractable hGC:FLAG ™ |
|---|---|---|
| *1 gm | 4–5 mg | 1.5 mg |
| 1.6 kg/plant | 6–8 gm | 2.4 gm |
| 6,000 PLANTS/ACRE (Standard field) | | |
| 9,600 kg | 38–48 kg | 14.4 kg |

*These estimations are based on slot blot westerns using anti-FLAG and crude extracts from 0.5 gm–50 gm of post-wounded tissue.

7. EXAMPLE 2

PRODUCTION AND PURIFICATION OF IDUA IN TRANSGENIC TOBACCO PLANTS

The subsections below describe the production of enzymatically active recombinant human α-L-iduronidase (IDUA) in transgenic tobacco plants.

7.1. CONSTRUCTION OF A PLANT TRANSFORMATION VECTOR CONTAINING AN IDUA EXPRESSION CONSTRUCT

7.1.1. IDUA EXPRESSION CONSTRUCT

The first step in the construction of the desired plant transformation vector was to generate the human IDUA coding region with appropriate flanking restriction site to facilitate fusion to specific plant promoters and insertion into plant transformation vectors. A full-length human IDUA cDNA clone was provided by E. Neufeld (University of California, Los Angeles). In this clone, the IDUA cDNA sequence was inserted into the EcoRI site of pBS plasmid (Moskowitz et al., 1992, FASEB J. 6:A77; Murray, 1987, Methods in Enzymol. 149:25–42). This IDUA cDNA sequence has been expressed in animal cell lines (Moskowitz et al., 1992, supra, 1987, supra) and shown to contained all the information necessary to produce enzymatically active IDUA (Murray, 1987, supra). The IDUA cDNA encodes a 653 amino acid protein (66 kDa) including the 26 amino-terminal signal peptide which is cleaved as it passes through the ER membrane. To aid in the insertion of the IDUA cDNA into the plant vector, unique flanking XbaI and SacI sites were introduced by PCR using 5'-primer ID1 and 3'-primer ID2, Pfu polymerase (Stratagene, La Jolla, Calif.); as shown in FIG. 12. The 1.9 kb fragment generated by PCR was purified by agarose gel electrophoresis, digested with XbaI and SacI, and ligated into pBS and pSP64polyA (Gibco, a vector for in vitro transcription/translation). The PCR-amplified IDUA coding sequence was sequenced prior to insertion into the expression constructs. The nucleotide and deduced amino acid sequences of the amplified IDUA coding sequence are shown in FIGS. 19 (SEQ ID NO:8) and 20 (SEQ ID NO:9), respectively. The PCR-amplified IDUA coding sequence differs from that originally published by E. Neufeld at positions 931 and 932. The PCR-amplified IDUA sequence has the dinucleotide CG instead of the original GC at those positions. Accordingly, the deduced amino acid sequence of the PCR-amplified IDUA has a glutamate, instead of a glutamine, residue at position 282. In vitro transcription of the PCR-amplified IDUA sequence in a pSP64polyA:IDUA vector and rabbit reticulocyte lysate-mediated in vitro translation of the resultant transcript produced protein having a molecular size expected for IDUA.

The PCR-amplified IDUA coding region was inserted downstream of two distinctly regulated plant promoters: 1) the MeGA promoter and 2) the $35S^{ENH}$ promoter. As discussed above, the MeGA promoter shows little or no expression in most plant tissues but is strongly inducible resulting in significant transgene product accumulation 12 to 48 hours after induction of the MeGA promoter. The $35S^{ENH}$ promoter is a widely used high-level constitutive promoter consisting of a modified CaMV 35S promoter containing double enhancer which is fused to a translational enhancer from the tobacco etch virus. See Cramer et al., 1996, "High-Level of Enzymatically Active Human Lysosomal Proteins in Transgenic Tobacco", *Transgenic Plants: A production System for Industrial and Pharmaceutical Proteins*, eds., Owens & Pen, John Wiley & Sons; Chrispeels, 1991, Annu. Rev. Plant Physiol. Plan. Biol. 42:21–53; and Haskins et al., 1979, Pediat. Res. 13:1294–1297. Each promoter was ligated as a HindIII-XbaI fragment upstream of the IDUA cDNA (see FIG. 12).

7.1.2. IDUA EXPRESSION/TRANSFORMATION VECTORS

During the subcloning and vector analysis steps, bacterial transformants having any vector containing the 5'-end of the IDUA cDNA were recovered at lower than expected frequencies. For example, multiple ligation and transformations of competent *E. coli* cells DH5α with pBs containing the 1.9 kb PCR amplified IDUA cDNA were required to generate fewer than 100 transformants. Among the 70 transformants analyzed by restriction analysis of the plasmid DNA, only 2 clones contained the proper sized 1.9 kb fragment. One of the two clones was sequenced and found to contain the complete IDUA coding sequence. Colony size of IDUA containing transformant was reduced. These reduced efficiencies were independent of plasmid vector, preserce or absence of plant promoter, IDUA expression (not fused to a bacterially active promoter) or bacterial host. Independent subcloning of the 3'-versus 5'-end of the IDUA cDNA localized an "obnoxious" region to the 5'-end of the IDUA sequence. DNA secondary structure or the high GC content of this region may cause intolerance in heterologous organisms. This effect by the 5'-end of the IDUA cDNA has also been noticed in yeast and animal cell expression systems. These limitations in transformation of the IDUA sequence, however, did not preclude successful isolation and characterization of the desired IDUA expression and transformation constructs.

For both promoter constructs, the promoter:IDUA cDNA fusions were excised as HindIII/SacI fragments and liglated into HindIII and SacI-digested pBIB-KAN (FIG. 12). pBIB-Kan is a large (>13 kb) plant transformation vector that provides a terminator/polyadenylation signal (pAnos) for the introduced transgene, a selectable marker (NPTII or kzinamycin resistance) for transformed plant cells, and T-DNA border sequences that demarcate the DNA to be transferred (Becker, 1990, Nucl. Acids Res. 18:203). The recombinant vectors were propagated in *E. coli* and fully characterized prior to transfer to *Agrobacterium tumefaciens*. A pBIB-KAN vector containing the MeGA:IDUA expression construct used in T-DNA transformation of plants is pCT22.

7.2. GENERATION OF TRANSGENIC TOBACCO CONTAINING THE IDUA CONSTRUCTS

Agrobacterium-mediated transformation was used to stably integrate the $35S^{ENH}$:IDUA and MeGA:IDUA constructs into the genome of tobacco. Approximately 80 leaf discs were excised from aseptically grown *Nicotiana tabacum* cvs. *Xanthi* seedlings for each gene construct and inoculated with suspension cultures of *A. tumefaciens* strains containing the IDUA expression/transformation vectors. Following a 48 hour co-cultivation period, the leaf discs were transferred to selection media containing kanamycin and hormones that promote shoot formation. Although numerous shoots (4–10 per disc) generally appear 2–3 weeks after transfer to selection media, the IDUA-transformed shoots appeared late, i.e., after 3–5 weeks, and were few in number (0–1 per disc). Induction of root formation was also delayed in the IDUA-transformed shoots compared to shoots containing other transgene constructs. A final yield of seven $35S^{ENH}$:IDUA and ten MeGA:IDUA plantlets were transferred to soil. Once in soil, all plants grew to maturity with normal morphology, flowering, and seed production. IDUA-expressing progenies showed slight retardation in early growth (FIG. 13B) but were indistinguishable in size and appearance from untransformed plants at full maturity.

7.3. SOUTHERN CHARACTERIZATION OF TRANSGENIC PLANTS

Transgenic plants were initially selected based on kanamycin resistance. The stable insertion of the MeGA:IDUA gene construct was confirmed by genomic Southern hybridization analysis. Total DNA was isolated from leaf tissue of nine transgenic plants and digested with HindIII, and analyzed by Southern hybridization using the IDUA cDNA as probe. The nine putative transformants analyzed showed one to three copies of the IDUA insert and no indication of rearrangements or deletions. This transgene copy number is typical of transgenic tobacco engineered with other constructs via Agrobacterium.

7.4. CHARACTERIZATION OF IDUA EXPRESSION IN TRANSGENIC PLANTS 7.4.1. IMMUNO-DETECTION OF IDUA PROTEIN IN PLANT EXTRACT

Antibodies made to the native and denatured IDUA from CHO cells were obtained from E. Kakkis (Harbor-UCLA Medical Center, Los Angeles, Calif.). By immuno-slot blot and SDS-PAGE Western analysis, the antibodies were found not to react with any proteins in untransformed or pBIB-Kan (transformed vector alone) transgenic tobacco tissue extracts from uninduced or induced leaf tissue. When purified IDUA from CHO cells was seeded to untransformed tobacco extracts, there was no diminution in the level of IDUA detected as compared to that detected in extraction buffer containing the same concentration of purified IDUA. This finding indicates that tobacco extract does not inhibit immuno-detection of IDUA.

Leaf tissues from seven independent transgenic plants were harvested, homogenized in 3X volume of extraction buffer (PBS with 0.1% Triton X100, 200 $\mu$M PMSF, 1 $\mu$M pepstatin, 4 $\mu$M leupeptin) and the extracts cleared of cell debris by centrifugation at 12,000×g for 30 min. Twenty-five $\mu$g of total soluble protein from each extract was heat-denatured and slotted onto OPTITRAN membrane (S&S). Purified IDUA protein in amounts ranging from 20 ng to 400 ng were added to the membrane to serve as comparison standards. Based on antibody detection using chemiluminescence, no immuno-reactive IDUA protein was found in the extracts of any of the $35S^{ENH}$:IDUA transgenic plants. This constitutive promoter also poorly expressed human protein C (<0.02% of soluble protein). Based on these findings, the $35S^{ENH}$:IDUA-containing plants were not analyzed further.

The MeGA promoter is inactive in tobacco leaves in the absence of induction. To obtain IDUA expression, leaves were harvested, induced by mechanical wounding and incubated at room temperature under high humidity (i.e., the wounded leaves are wrapped in moist filter paper in sealed bags or layered in a container with buffer gently swirled over the tissue) to allow de novo synthesis of the transgene product. In an initial screen of ten MeGA:IDUA-containing plants, tissue extracts were used for immunodot-blot analyses (see above). The extracts showed little or no IDUA content for all plants. Later analyses revealed that IDUA was secreted from the leaves and leached out onto the filter paper during the incubation step. This was somewhat surprising because recovery of extracellular proteins from intact leaf generally requires vacuum-induced buffer infiltratior of the leaf (see Parent & Asselin, 1987, Can. J. Bot. 62:564–569; Regalado & Ricardo, 1996, Plant Physiol. 110:227–232). As described below, the expression procedure was subsequently modified to include a post-induction incubation step that involved gentle rotation of buffer over the wounded tissue, which permitted recovery of IDUA protein and activity in the incubation buffer. Subsequent analyses were focused primarily on one plant, IDUA-9 also known as CT40-9, since preliminary tests show detectable levels of IDUA activity and anti-IDUA immuno-reactive material. IDUA-9 contains 3 copies of the MeGA:IDUA construct.

7.4.2. NORTHERN ANALYSIS SHOWS ACTIVATION OF THE MEGA:IDUA TRANSGENE

In order to demonstrate induction of the MeGA promoter and accumulation of IDUA mRNA, total RNA was isolated (Rutter, 1981, J. Biol. Chem. 91:468–478) from IDUA-9 leaves before and after induction. As shown in FIG. 14A, IDUA mRNA of the expected size (approximately 2.2 kb) was detected at low basal levels in uninduced tissue and showed a marked increase at 8 hrs post-induction and reached a maximum level at 27 hrs post-induction. This pattern is similar to transgene induction kinetics seen with other MeGA-driven constructs (e.g., hGC:FLAG™). The smaller hybridizing RNA species also accumulated after induction. Analogous lower molecular weight RNAs have not been detected in hGC:FLAG™ expressing plants and may be unique to the IDUA-9 plant or a consequence of the IDUA sequence.

7.4.3. WESTERN ANALYSIS OF HUMAN IDUA LOCALIZED TO TOBACCO

The induced IDUA-9 tissues were also used for protein extracts. Western blot analysis showed CHO-derived IDUA and IDUA from tobacco tissue migrated very similarly in SDS-PAGE (FIG. 14B). The IDUA (92 kD) from IDUA-9 tobacco extract migrated slightly faster than secreted IDUA from CHO cells. This presumably is due to differences in glycan composition. However, the similarity in size suggests that the tobacco produced recombinant IDUA was also glycosyleated.

7.4.4. IDUA SYNTHESIZED IN TRANSGENIC TOBACCO IS SECRETED

As discussed above, CHO cells secrete recombinant IDUA into the media. To determine if tobacco also secrete recombinant IDUA into the media, leaf tissue from transgenic IDUA-7, -8 and -9 plants were induced for 0 to 34 hrs and placed in a plastic petri dish with incubation buffer (PBS). At 0 hr, incubation buffer was used to wash the induced tissue and the wash stored frozen. Fresh buffer was added to the induced tissue and incubated at room temperature. At 8 hrs, the buffer was removed and frozen. Fresh buffer was added to the induced tissue and incubated further. The buffer was removed at 24 hrs post-induction. Fresh buffer was added to the induced tissue and further incubated. The final incubation buffer was removed 34 hrs post-induction and a tissue extract was prepared from the incubated leaf tissue. Fifty $\mu$l of each incubation buffer and tissue extract was boiled and slotted onto OPTITRAN membrane. A range of control IDUA protein from 0 to 40 ng was also blotted and IDUA was detected using anti-IDUA antibodies. As shown in FIG. 15, IDUA protein was present in the incubation buffer following induction in all three transgenic tissue analyzed. This indicates that transgenic tobacco secrete IDUA after synthesis.

7.4.5. THE TOBACCO-SYNTHESIZED IDUA IS ENZYMATICALLY ACTIVE

One of the most critical factors in assessing the utility of plant-synthesized recombinant IDUA is whether the IDUA is enzymatically active. Enzyme activity of human lysosomal hydrolases requires appropriate glycosylation and folding and heterologous expression systems often result in endoplasmic reticulum-localized degradation or accumulation of insoluble and inactive aggregates. To determine whether the recombinant IDUA synthesized in transgenic leaves has enzymatic activity, a sensitive fluorometric assay using the substrate, 4-Methylumbelliferyl-α-L-iduronide (4-MUI) (Calbiochem, LaJolla, Calif.) was used (see Neufeld, E. F., 1991, Ann. Rev. Biochem. 60:257–280). Untransformed tobacco extracts were shown to contain no endogenous IDUA activity. When CHO-derived recombinant IDUA was seeded into crude extracts of untransformed tobacco leaves, no detectable inhibition of activity was found. When the tissue extracts from IDUA-9 transgenic plant were assayed, the extracts showed IDUA activity at reproducible but at relatively low levels (0.2 to 0.4 nmole 4-MU/hr/gm tissue). This confirms that tobacco has all the necessary machinery to synthesize and process IDUA into an active form. Consistent with IDUA distribution shown by immuno-detection, significantly higher IDUA activities were detected in the secreted fraction as described below.

7.4.6. SECRETION AND RECOVERY OF TOBACCO-SYNTHESIZED RECOMBINANT IDUA

Significant portion of the recombinant IDUA produced in transgenic tobacco was recovered in the incubation buffer following induction of the MeGA:IDUA gene construct (FIG. 15). Localization of the majority of active IDUA after induction and incubation was determined. This was done by comparing the IDUA activity and anti-IDUA immunoreactivity of tissue extract with those of the incubation buffer. As shown in FIG. 16, there was much higher levels of IDUA activity in the incubation buffer than in the tissue extract after induction and incubation. Moreover, the IDUA activity in the incubation buffer showed strong correlation with the the amount of anti-IDUA immuno-reactive material found in the incubation buffer, as reveal by the data presented in FIG. 15. Thus, IDUA-expressing transgenic tobacco secrete most of its active IDUA (about 67%) into the incubation buffer after induction and incubation.

Based on activity assays and Western analysis, the specific activity of secreted IDUA was estimated to be about 64 U/$\mu$g protein. In comparison, purified IDUA enzyme from engineered CHO cells has a specific activity of about 242 U/$\mu$g protein.

Variation in transgene expression levels is very common in transgenic plants due to "positional" effects caused by the site of transgene insertion within the host genome. The IDUA activity levels in three independent IDUA-expressing transgenic plants (i.e., IDUA-7, IDUA-8 and IDUA-9) were examined. Among these transgenic plants, IDUA-9 has the highest IDUA activity (FIG. 17). The relative amount of active IDUA remaining in the cell, as reflected by the activity present in tissue extract, after 34 hrs of incubation ranged from 14% to 35% of the total activity (FIG. 17).

The above-identified three transgenic plants were identified in a screen of about fifty independently transformed plants. This is a relatively small scale screen. It is reasonable to expect that larger scale Ecreenings of IDUA-engineered plants will yield plants that produce active IDUA at levels higher than those of the plantes disclosed herein.

7.4.7. PURIFICATION AND YIELD OF IDUA FROM TRANSGENIC TOBACCO

The yield of recombinant IDUA from IDUA-9 was estimated to be about 6 $\mu$g/gm fresh tissue. This estimate was based on the material present in the incubation buffer after 34 hrs of incubation (see FIG. 18). However, neither the induction nor the IDUA recovery procedure used was optimized. Thus, it is likely that higher IDUA yields may be acheived through optimization of induction and recovery procedures. It should be noted that the transgenic tobacco plants yielded an average of greater than 1 kg fresh weight of leaf at maturity, and that leaves can be periodically harvested from greenhouse-grown plants for over an year. Accordingly, cultivation of transgenic tobacco plants either in the field of the greenhouse offers a convenient and effective means for producing large amounts of IDUA.

8. EXAMPLE 3

PRODUCTION OF TRANSGENIC TOBACCO PLANTS CONTAINING AN UNMODIFIED hGC EXPRESSION CONSTRUCT

A 3' end segment of the hGC coding sequence was PCR-amplified from the cDNA clone in *E. coli* ATCC65696

(see Section 6.1.1., supra) using as the 5' primer GC23 oligo, 5'GCCTATGCTGAGCACAAGTTACAG3' (SEQ ID NO:11), whose 5' end corresponds to nucleotide 894 of the hGC:FLAG sequence shown in FIG. 9, and as the 3' primer GC37 oligo, whose complementary strand has the sequence 5' TTCCTTGAGCTCGtcaCTGGCGACGCCACAGGTA3' (SEQ ID NO:12), a SacI restriction site is shown with an underline and a stop codon that is in-frame to the amplified hGC coding sequence is shown in lower case. The site of the 5' primer in the hGC coding sequence is 5' upstream of a SalI restriction site. Accordingly, the amplified DNA was cut with SalI and SacI, and the SalI/SacI fragment containing the 3' end of hGC coding sequence was inserted into the pBS intermediate vector containing the MeGA:hGC:FLAG™ expression construct (see FIG. 1 and Section 6.1.2., supra) which had been cut with SalI and SacI. Clones were identified that had replaced the 3' end of the MeGA:hGC-:FLAG™ construct with the 3' end of hGC coding sequence yielding a MeGA:hGC expression construct. This construction eliminated the ten amino acid addition at the carboxyl terminal and corrected the amino acid substitution at residue 545 in the hGC:FLAG™ fusion, and thereby reconstructing an unmodified hGC coding sequenze. The MeGA:hGC expression construct was excised from the pBS intermediate vector by SacI digestion and inserted into pBIB-KAN to form the transformation vector pCT54. Ak schematic of the construction of the pCT54 vector is shown in FIG. 21.

Agrobacterium containing pCT54 was used to tranformed plants and transgenic tobacco plants containing the MeGA-:hGC expression construct were produced according to procedures described aboveTransgenic tobacco plants containing the MeGA:hGC expression construct were identified atnd assigned the designations CT54-1 to -40. Analyses of hGC enzymatic activity and presence of hGC in the induced tissues of transgenic plants are carried out using the enzymatic assay described in Section 6.2.5. and the Western blot analysis using anti-hGC antibodies described in Section 6.2.6. Purification of the hGC produced in transgenic tobacco tissue is carried out using the procedure described in Section 6.3., except the anti-FLAG™ affinity chromatography step was omitted, which procedure is further modified accordingly to strategies and methods known in the art for purifying the hGC enzyme.

9. DEPOSIT OF BIOLOGICAL MATERIALS

The following biological materials have been deposited with the American Type Culture Collection (ATCC) at 12301 Parklawn Drive, Rockville, Md. 20852, in compliance with the requirements of the Budapest Treaty On The International Recognition Of The Deposit Of Microorganisms For The Purpose Of Patent Procedure, on the dates and were assigned the ATCC accession numbers indicated below.

| Deposited Material | Deposit Date | Accession No. |
|---|---|---|
| DNA of pCTPro1:hGC:FLAG | Sept. 14, 1995 | 97277 |
| seeds of tobacco plant hGC X-11 | Sept. 14, 1995 | 97275 |
| seeds of tobacco plant hGC X-27 | Sept. 14, 1995 | 97276 |
| DNA of pCT22 | Aug. 30, 1996 | 97701 |
| seeds of tobacco plant CT40-9 | Aug. 30, 1996 | 97700 |
| DNA of pCT54 | Oct. 17, 1996 | 97770 |

The present invention is not to be limited in scope by the biological material deposited since the deposited embodiments are intended as illustrations of the individual aspects of the invention, and any biological material, or constructs which are functionally equivalent are within the scope of this invention. Indeed, various modifications of the invention in addition to those shown and described herein will become apparent to those skilled in the airt from the foregoing description and accompanying drawings. Such modifications are intended to fall within the scope of the appended claims.

Various references are cited herein; these are incorporated by reference in their entirety.

What is claimed is:

1. A method for producing a lysosomal enzyme which is enzymatically active, comprising:

recovering the lysosomal enzyme from (i) a transgenic plant cell or (ii) a cell, tissue or organ of a transgenic plant, which transgenic plant cell or plant is transformed or transfected with a recombinant expression construct comprising a nucleotide sequence encoding the lysosomal enzyme and a promoter that regulates expression of the nucleotide sequence so that the lysosomal enzyme is expressed by the transgenic plant cell or plant.

2. The method according to claim 1, in which the promoter is an inducible promoter.

3. The method according to claim 2, in which the inducible promoter is induced by mechanical gene activation.

4. The method according to claim 3, in which the inducible promoter comprises SEQ ID NO:5.

5. The method according to claim 2, which is carried out with the transgenic plant and additionally comprises a step of inducing the inducible promoter before or after the transgenic plant is harvested, which inducing step is carried out before recovering the lysosomal enzyme from the cell, tissue or organ of the transgenic plant.

6. The method according to claim 1, in which the lysosomal enzyme is a modified lysosomal enzyme which is enzymatically active and comprises:

(a) an enzymatically-active fragment of a human or animal lysosomal enzyme;

(b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions.

7. The method according to claim 6, in which the modified lysosomal enzyme comprises a signal peptide or detectable marker peptide at the amino or carboxyl terminal of the modified lysosomal enzyme.

8. The method according to claim 7, in which the modified lysosomal enzyme is recovered from (i) the transgenic plant cell or (ii) the cell, tissue or organ of the transgenic plant by reacting with an antibody that binds the detectable marker peptide.

9. The method according to claim 7, in which the antibody is a monoclonal antibody.

10. The method according to claim 7, in which the detectable marker peptide comprises SEQ ID NO:10.

11. The method according to claim 6, in which the modified lysosomal enzyme comprises:

(a) an enzymatically-active fragment of an α-N-acetylgalactosaminidise, acid lipase, α-galactosidase, glucocerebrosidase, α-L-iduronidase, iduronate sulfatase, α-mannosidase or sialidase;

(b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, -iduronate sulfatase, α-mannosidase, sialidasc or (a) having one or more naturally-occurring amino acid additions, deletions or substitutions.

12. The method according to claim 11, in which the modified lysosomal enzyme comprises:

(a) an enzymatically-active fragment of a human glucocerebrosidase or human α-L-iduronidase enzyme;

(b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions.

13. The method according to claim 6, in which the modified lysosomal enzyme is a fusion protein comprising:

(I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I); and the method comprises:

(i) recovering the fusion protein from the transgenic plant cell, or the cell, tissue or organ of the transgenic plant;

(ii) treating the fusion protein with a substance that cleaves the cleavable linker so that (I) is separated from the cleavable linker and any sequence attached thereto; and (iii) recovering the separated (I).

14. The method according to claim 1, in which the transgenic plant is a transgenic tobacco plant.

15. The method according to claim 1, in which the lysosomal enzyme is a human or animal lysosomal enzyme.

16. The method according to claim 15, in which the lysosomal enzyme is an α-N-acetylgalactosaminidase, acid lipase, α-galactosidase, glucocerebrosidase, α-L-iduronidase, iduronate sulfatase, α-mannosidase or sialidese.

17. The method according to claim 16, in which the lysosomal enzyme is a human glucocerebrosidase or human α-L-iduronidase.

18. The method according to claim 1, in which the organ is leaf, stem, root, flower, fruit or seed.

19. A recombinant expression construct comprising a nucleotide sequence encoding a lysosomal enzyme and a promoter that regulates the expression of the nucleotide sequence in a plant cell.

20. The recombinant expression construct of claim 19, in which the promoter is an inducible promoter.

21. The recombinant expression construct of claim 20, in which the inducible promoter is induced by mechanical gene activation.

22. The recombinant expression construct of claim 20, in which the inducible promoter comprises SEQ ID NO:5.

23. The recombinant expression construct of claim 19, in which the lysosomal enzyme is a modified lysosomal enzyme which is enzymatically active and comprises:

(a) an enzymatically-active fragment of a human or animal lysosomal enzyme;

(b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions.

24. The recombinant expression construct of claim 23, in which the modified lysosomal enzyme comprises a signal pertide or detectable marker peptide at the amino or carboxyl terminal of the modified lysosomal enzyme.

25. The recombinant expression construct of claim 24, in which the detectable marker peptide comprises SEQ ID NO:10.

26. The recombinant expression construct of claim 23, in which the modified lysosomal enzyme comprises:

(a) an enzymatically-active fragment of an α-N-acetylgalactosaminidase, acid lipase, α-galactosidase, glucocerebrosidase, α-L-iduronidase, iduronate sulfatase, α-mannosidase or sialidase;

(b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions.

27. The recombinant expression construct of claim 26, in which the modified lysosomal enzyme comprises:

(a) an enzymatically-active fragment of a human glucocerebrosidase or human α-L-iduronidase enzyme;

(b) the human glucocerebrosidase or human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions.

28. The expression construct of claim 23, in which the modified lysosomal enzyme is a fusion protein comprising (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I).

29. The recombinant expression construct of claim 19, in which the lysosomal enzyme is a human or animal lysosomal enzyme.

30. The recombinant expression construct of claim 29, in which the lysosomal enzyme is an α-N-acetylgalactosaminidase, acid lipase, α-galactosidase, glucocerebrosidase, α-L-iduronidase, iduronate sulfatase, α-mannosidase or sialidase.

31. The recombinant expression construct of claim 30, in which the lysosomal enzyme is a human glucocerebrosidase or human α-L-iduronidase.

32. A plant transformation vector comprising the recombinant expression construct of claim 19, 20, 24, 29, 31, 23, 27 or 28.

33. A plant which is transformed or transfected with the recombinant expression construct of claim 19, 20, 24, 29, 31, 23, 27 or 28.

34. A plant cell, tissue or organ which is transformed or transfected with the recombinant expression construct of claim 19, 20, 24, 29, 31, 23, 27 or 28.

35. A plant transfection vector comprising the recombinant expression construct of claim 19, 20, 24, 29, 31, 23, 27 or 28.

36. A plasmid comprising the recombinant expression construct of claim 19, 20, 24, 29, 31, 23 or 27.

37. A plasmid CTPro1:hGC:FLAG having the ATCC accession number 97277.

38. A plasmid pCT22 having the ATCC accession nunber 97701.

39. A plasmid pCT54 having the ATCC accession number 97770.

40. A transgenic plant or plant cell capable of producing a lysosomal enzyme which is enzymatically active, which transgenic plant or plant cell is transformed or transfected with a recombinant expression construct comprising a nucleotide sequence encoding a lysosomal enzyme and a promoter that regulates expression of the nucleotide sequence in the transgenic plant or plant cell.

41. The transgenic plant or plant cell of claim 40, in which the promoter is an inducible promoter.

42. The transgenic plant or plant cell of claim 41, in which the inducible promoter is induced by mechanical gene activation.

43. The transgenic plant or plant cell of claim 42, in which the inducible promoter comprises SEQ ID NO:5.

44. The transgenic plant or plant cell of claim 40, in which the lysosomal enzyme which is a modified lysosomal enzyme which is enzymatically active and which comprises:

(a) an enzymatically-active fragment of a human or animal lysosomal enzyme;

(b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions.

45. The transgenic plant or plant cell of claim 44, in which the modified lysosomal enzyme comprises a signal peptide or detectable marker peptide at the amino or carboxyl terminal of the modified lysosomal enzyme.

46. The transgenic plant or plant cell of claim 45, in which the detectable marker peptide comprises SEQ ID NO:10.

47. The transgenic plant or plant cell of claim 44, in which the modified lysosomal enzyme comprises:

(a) an enzymatically-active fragment of an α-N-acetylgalactosaminidase, acid lipase, α-galactosidase, glucocerebrosidase, α-L-iduronidase, iduronate sulfatase, α-mannosidase or sialidase;

(b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions.

48. The transgenic plant or plant cell of claim 47, in which the modified lysosomal enzyme comprises:

(a) an enzymatically-active fragment of a human glucocerebrosidase or human α-L-iduronidase enzyme;

(b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions.

49. The transenic plant or plant cell of claim 44, in which the modified lysosomal enzyme is a fusion protein comprising:

(I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I).

50. The transgenic plant or plant cell of claim 40, in which the transgenic plant or plant cell is a transgenic tobacco plant or tobacco cell.

51. The transgenic plant or plant cell of claim 40, in which the lysosomal enzyme is a human or animal lysosomal enzyme.

52. The transgenic plant or plant cell of claim 51, in which the lysosomal enzyme is an α-N-acetylgalactosaminidase, acid lipase, α-galactosidase, glucocerebrosidase, α-L-iduronidase, iduronate sulfatase, α-mannosidase or sialidase.

53. The transgenic plant or plant cell of claim 52, in which the lysosomal enzyme is a human glucocerebrosidase or human α-L-iduronidase.

54. A leaf, stem, root, flower or seed of the transgenic plant of claim 40, 41, 45, 50, 51, 53, 44, 48 or 49.

55. A seed of plant line hGC X-11, which seed has the ATCC Accession No. 97275.

56. A seed of plant line hGC X-27, which seed has the ATCC Accession No. 97276.

57. A seed of plant line CT40-9, which seed has the ATCC Accession No. 97700.

58. A plant grown from the seed of claim 55, 56 or 57.

59. A lysosomal enzyme which is enzymatically active and is produced according to a process comprising:

recovering the lysosomal enzyme from (i) a transgenic plant cell or (ii) a cell, tissue or organ of a transgenic plant which transgenic plant cell or plant is transformed or transfected with a recombinant expression construct comprising a nucleotide sequence encoding the lysosomal enzyme and a promoter that regulates expression of the nucleotide sequence so that the lysosomal enzyme is expressed by the transgenic plant cell or plant.

60. The lysosomal enzyme of claim 59, in which the promoter is an inducible promoter.

61. The lysosomal enzyme of claim 60, in which the inducible promoter comprises SEQ ID NO:5.

62. The lysosomal enzyme of claim 60, which process is carried out with the transgenic plant and additionally comprises a step of inducing the inducible promoter before or after the transgenic plant is harvested, which inducing step is carried out before recovering the lysosomal enzyme from the cell, tissue or organ of the transgenic plant.

63. The lysosomal enzyme of claim 59, which is a modified lysosomal enzyme which is enzymatically active and comprises:

(a) an enzymatically-active fragment of a human or animal lysosomal enzyme;

(b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid, additions, deletions or substitutions.

64. The lysosomal enzyme of claim 63, in which the modified lysosomal enzyme comprises a signal peptide or detectable marker peptide at the amino or carboxyl terminal of the modified lysosomal enzyme.

65. The modified lysosomal enzyme of claim 64, in which the detectable marker peptide comprises SEQ ID NO:10.

66. The lysosomal enzyme of claim 63, in which the modified lysosomal enzyme comprises:

(a) an enzymatically-active fragment of an α-N-acetylgalactosaminidase, acid lipase, α-galactosidase, glucocerebrosidase, α-L-iduronidase, iduronate sulfatase, α-mannosidase or sialidase;

(b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfazase, α-mannosidase, sialidase or (a) having one or more naturally-occurring amino acid additions, deletions or substitutions.

67. The lysosomal enzyme of claim 66, in which the modified lysosomal enzyme comprises:

(a) an enzymatically-active fragment of a human glucocerebrosidase or human α-L-iduronidase enzyme;

(b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substiu-tions.

68. The lysosomal enzyme of claim 63, in which the modified lysosomal enzyme is a fusion protein comprising:

(I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I).

69. The lysosomal enzyme of claim 59, in which the transgenic plant is a transgenic tobacco plant.

70. The lysosomal enzyme of claim 39, in which the lysosomal enzyme is a human or animal lysosomal enzyme.

71. The lysosomal enzyme of claim 70, in which the lysosomal enzyme is an α-N-acetylgalactosaminidase, acid lipase, α-galactosidase, glucocerebrosidase, α-L-iduronidase, iduronate sulfatase, α-mannosidase or sialidase.

72. The lysosomal enzyme of claim 71, in which the lysosomal enzyme is a human glucocerebrosidase or human α-L-iduronidase.

73. The lysosomal enzyme of claim 59, in which the organ is leaf, stem, root, flower, fruit or seed.

* * * * *